(12) United States Patent
Voegele et al.

(10) Patent No.: US 7,861,893 B2
(45) Date of Patent: Jan. 4, 2011

(54) ADHESIVE DISPENSER FOR SURGERY

(75) Inventors: James W. Voegele, Cincinnati, OH (US); Jessica M. Liberatore, Marlboro, NJ (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1082 days.

(21) Appl. No.: 11/558,686

(22) Filed: Nov. 10, 2006

(65) Prior Publication Data

US 2008/0121657 A1    May 29, 2008

(51) Int. Cl.
*B67D 7/70* (2010.01)
*A61M 37/00* (2006.01)

(52) U.S. Cl. .............. 222/137; 222/145.6; 222/261; 222/309; 604/82; 604/91; 604/232

(58) Field of Classification Search .......... 222/137, 222/145.6, 145.5, 135, 334, 309, 258, 261, 222/262, 263; 604/82, 83, 85, 86, 87, 88, 604/89, 90, 91, 92, 146, 191, 232–235, 68–72, 604/20–24
See application file for complete search history.

(56) References Cited

U.S. PATENT DOCUMENTS 3,223,083 A * 12/1965 Cobey ................. 606/92
5,443,183 A * 8/1995 Jacobsen et al. ........ 222/145.6
6,047,861 A * 4/2000 Vidal et al. ............. 222/137
6,547,467 B2   4/2003 Quintero
6,960,340 B2  11/2005 Rowe et al.
2002/0165483 A1* 11/2002 Miller et al. ............ 604/82
2002/0198490 A1* 12/2002 Wirt et al. .............. 604/82
2003/0023202 A1*  1/2003 Nielson ................. 604/80
2003/0050597 A1*  3/2003 Dodge et al. ............ 604/82
2004/0190975 A1   9/2004 Goodman et al.

* cited by examiner

*Primary Examiner*—Kevin Shaver
*Assistant Examiner*—Stephanie E Williams
(74) *Attorney, Agent, or Firm*—Frost Brown Todd LLC

(57) ABSTRACT

A number of surgical devices for the mixing and dispensement of a dual component surgical adhesive onto tissue are described. The surgical devices can provide adhesive storage chambers for the adhesive components within the surgical device and can have removable cartridges that draw and mix and apply the adhesive onto tissue. The removable cartridges can be easily replaced when clogged with set adhesive. Alternately, an adhesive dispensing device can comprise an adhesive dispensing gun containing the dual components of the adhesive and a plurality of rotatable orifices that can dispense the adhesive. One orifice can be selected and aligned with the adhesive dispensing gun to mix and apply the adhesive onto tissue. A fresh orifice can be rotated into alignment with the gun should a prior orifice become blocked.

18 Claims, 20 Drawing Sheets

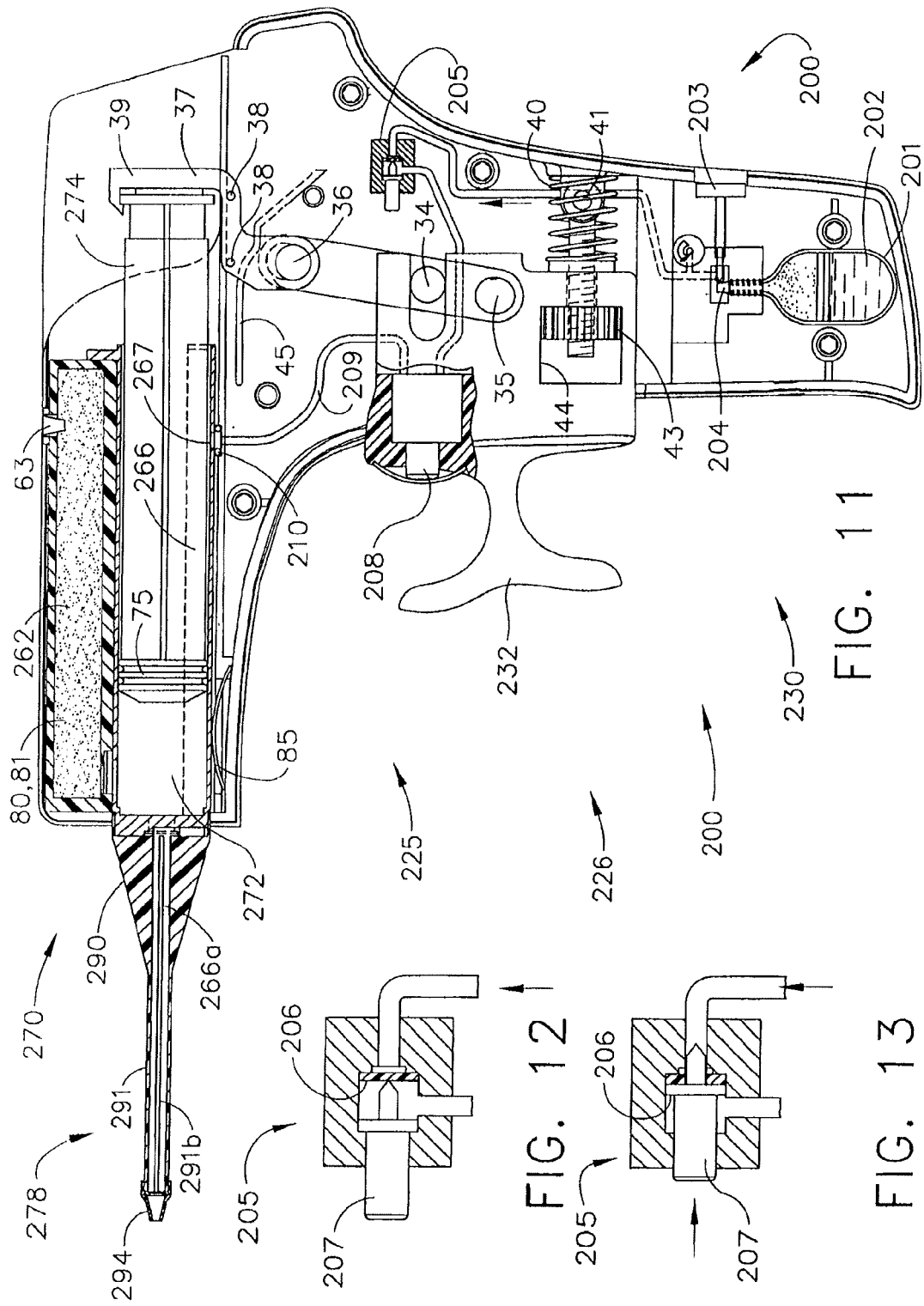

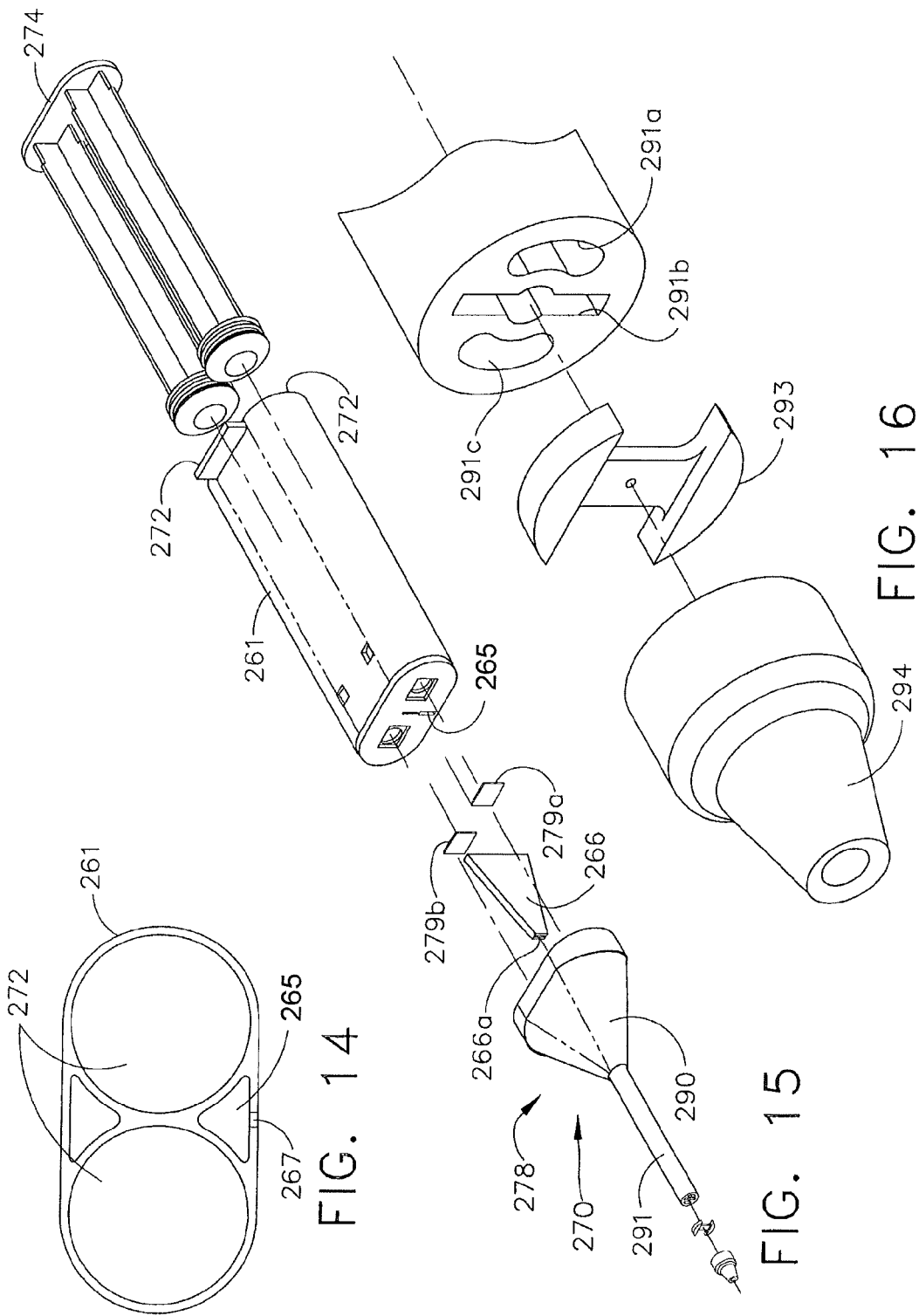

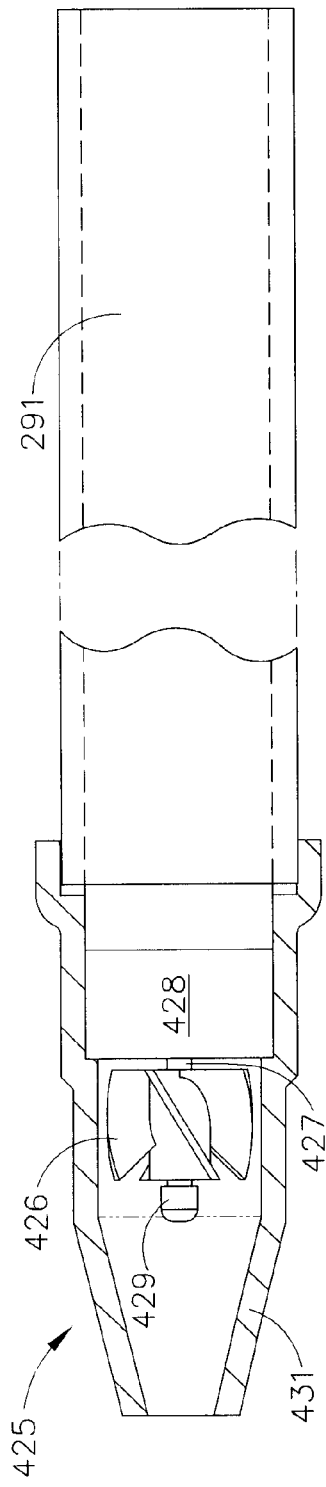
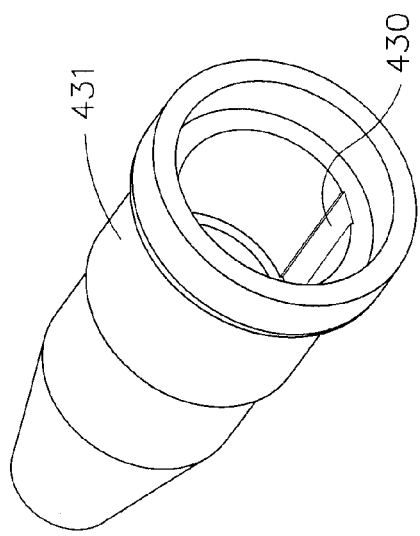
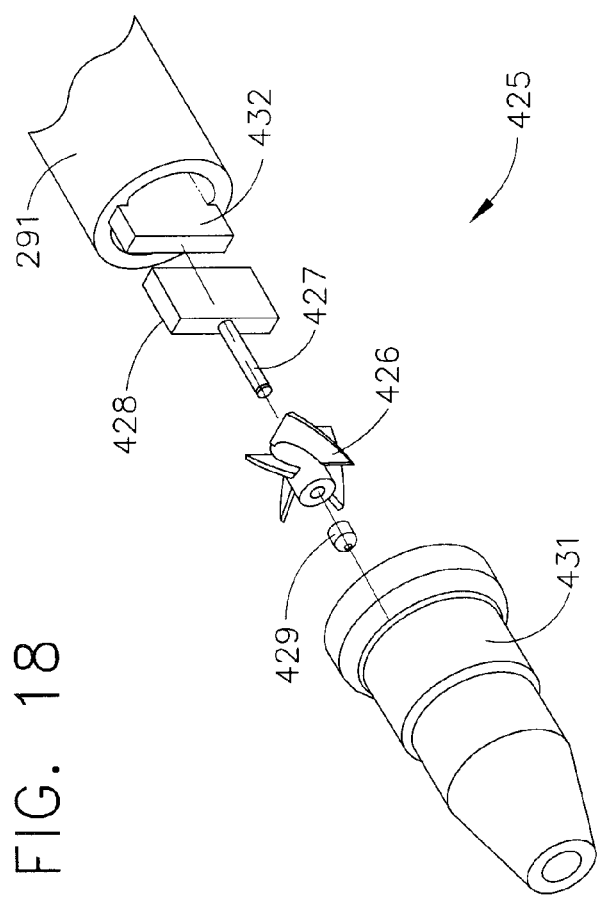
FIG. 18
FIG. 19
FIG. 20

ADHESIVE DISPENSER FOR SURGERY

FIELD OF THE INVENTION

The present invention relates, in general, to surgical devices for fastening tissue and in particular, to adhesive dispensing fastening devices.

BACKGROUND OF THE INVENTION

Adhesives can be used in surgery for wound repair and as attachment devices to join tissue. For surgery, a rapid setting time or polymerization time is needed to reduce time and surgical costs. Rapid setting time is a dual edge sword. On one hand, rapid setting times can make an adhesive useful, on the other hand, the nozzle of the glue dispensing device can become blocked from a brief period of inactivity.

Adhesives can be single part or dual part. Of interest are dual part adhesives that can be stored in two separate chambers and brought together and mixed just before being applied to tissue.

Closure Medical is conducting an FDA clinical trial using a cyanoacrylate adhesive as an internal vascular tissue sealant and internal surgical adhesive. Some adhesives such as the cyanoacrylates, stick well to tissue. Additionally, the adhesives can be biocompatible, bioabsorbable, and/or flexible, inside the body. Cyanoacrylate adhesives are described in United States Application 20040190975 by Goodman et al. which is herein incorporated by reference in its entirety.

With the high cost of surgery and the ever increasing pressures to drop the cost of surgery, there is a need for a surgical adhesive dispensing device that can dispense all of the adhesive, or can store unused adhesives for some period of time Consequently, a significant need exists for a surgical adhesive dispensing device that can reliably dispense adhesive, is low in cost, can reduce the possibility of blocking the adhesive dispensing nozzle, and can dispense the entire amount of the adhesive without requiring disposal of unused portions of adhesive.

BRIEF SUMMARY OF THE INVENTION

The invention overcomes the above-noted and other deficiencies of the prior art by providing a surgical device for the mixing and dispensing of a dual component surgical adhesive onto tissue. The surgical device comprises a handle and a first chamber containing a first adhesive component and a second chamber containing a second adhesive component. The first chamber and the second chamber are located within the handle.

A replaceable cartridge is removably attached to the handle and has an empty third chamber and an empty a fourth chamber and a mixing nozzle. The mixing nozzle is operably coupled to the third chamber and the fourth chamber, wherein when the replaceable cartridge is removably attached to the handle, the third chamber is operably attached to the first chamber and the fourth chamber is operably attached to the second chamber.

A firing mechanism is provided within the handle and operably coupled to the replaceable cartridge when the cartridge is removably attached to the handle. When the firing mechanism is actuated, a portion of the first adhesive component is drawn from the first chamber and into the third chamber, and a portion of the second adhesive component is drawn from the second chamber and into the fourth chamber. And, the first portion of adhesive and the second portion of adhesive are mixed and ejected from the nozzle onto tissue.

In one aspect of the invention, a second surgical device for the mixing and dispensing of a dual component surgical adhesive onto tissue is provided. The second surgical device comprises a handle and a replaceable cartridge removably attached to the handle. The replaceable cartridge has a first chamber containing a first adhesive component, a second chamber containing a second adhesive component, a third chamber for the receipt of the first adhesive component, and a fourth chamber for the receipt of the second adhesive component. A mixing nozzle is provided for the mixing and dispensing of the first adhesive component and the second adhesive component.

A firing mechanism is provided within the handle to draw the adhesive from the first and second chambers and into the third and fourth chambers, and then eject and mix the adhesive components from the nozzle.

In another aspect of the invention, a third surgical device for the mixing and dispensing of a dual component surgical adhesive onto tissue is provided. The surgical device has a handle having a first chamber containing a first adhesive component and a first exit port, and a second chamber containing a second adhesive component and having a second adhesive exit port. A firing mechanism is located in the handle and is operably coupled to the first chamber and the second chamber to disperse adhesive from the first exit port and the second exit port.

A nozzle assembly is rotatably attached to the handle and contains a plurality of adhesive orifices therein. Each of the adhesive orifices has an adhesive component mixer and is selectively alignable with the first exit port and the second exit port of the handle. Wherein when an orifice is aligned with the first exit port and the second exit port and the firing mechanism is actuated, the first adhesive component and the second adhesive component flow from the first exit port and the second exit port and are mixed in and dispersed from the selectively aligned orifice onto tissue.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 11 is a side view of a second alternate actuator handle assembled with an empty gas assist cartridge to create a second alternate adhesive dispensing device having a gas assisted mixing of the adhesive components.

FIG. 12 is a side view of a frangible seal to prevent gas from being dispensed until a firing trigger is actuated.

FIG. 13 is a side view of the frangible seal of FIG. 12 after the firing trigger is actuated and the frangible seal is breached.

FIG. 14 is a cross sectional end view of the empty gas assist cartridge of FIG. 11.

FIG. 15 is an isometric exploded view of the empty gas assist cartridge of FIG. 11.

FIG. 16 is an isometric exploded view of a gas assisted mixing nozzle of the empty gas assist cartridge of FIG. 15.

FIG. 18 is across sectional view of an alternate nozzle suitable for any alternate embodiments above having a rotating mixer blade to mix the adhesive components.

FIG. 19 is an isometric exploded view of the alternate nozzle of FIG. 18 showing the rotating mixer blade.

FIG. 20 is an isometric view into an end piece of the alternate nozzle of FIG. 19.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

During surgery, a variety of fasteners are typically used to approximate a wound by bringing two sides of tissue together in apposition to promote healing across the wound. Adhesives can also be used as a surgical fastener or as a wound repair medium. For surgery, two part adhesives can be used. Adhesives that have the rapid set time needed for surgery can be prone to blockage of the surgical dispensing device and result in surgeon frustration, unused adhesive and increased cost. Alternate designs for an adhesive dispensing device can eliminate some of these issues.

Replaceable Empty Cartridge Adhesive Dispensing Device.

Figure 3:
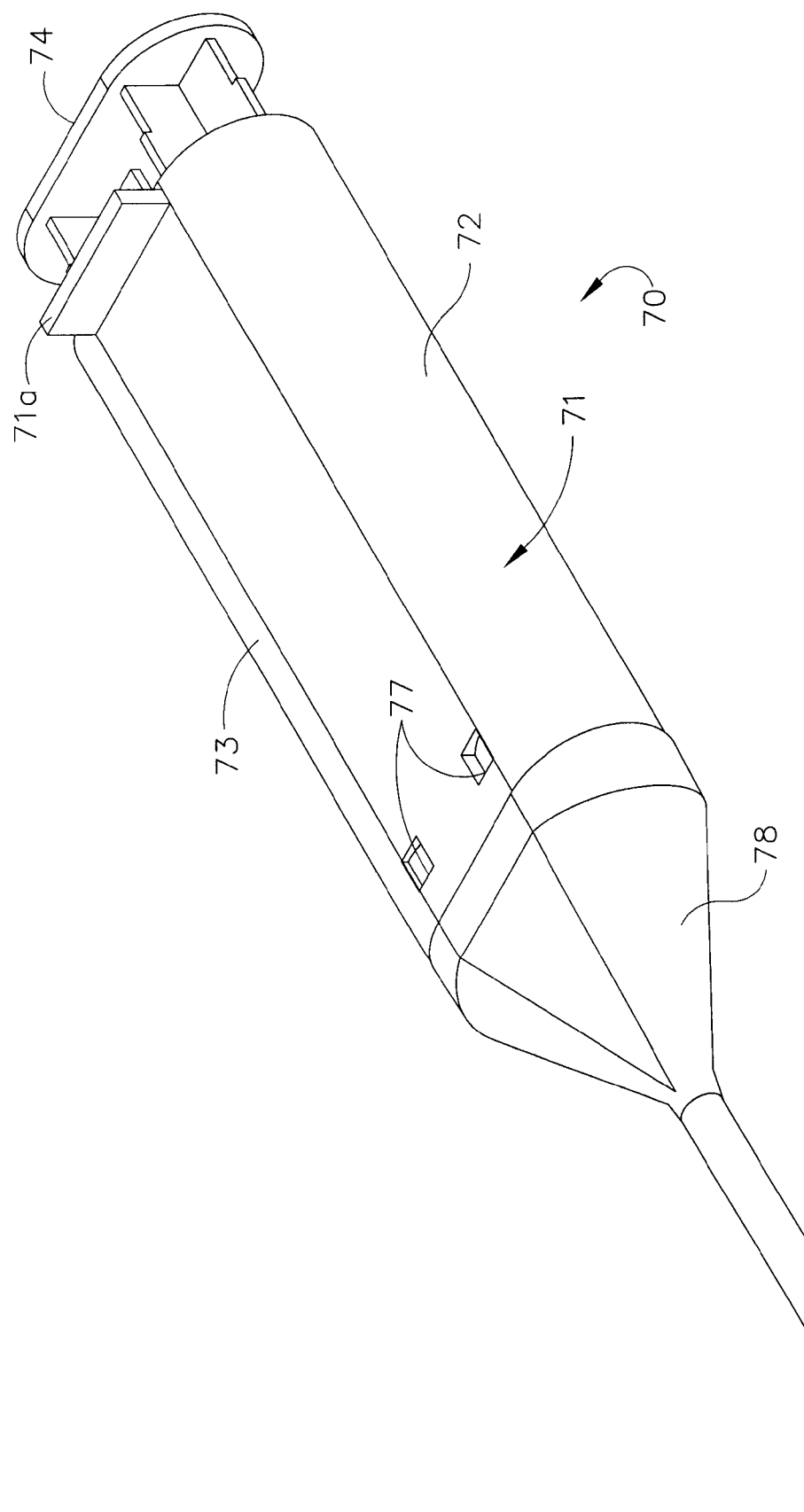
FIG. 3 is an isometric view of a replaceable empty cartridge mountable within the actuator handle of FIG. 2 to form the adhesive dispensing device.
Figure 4:
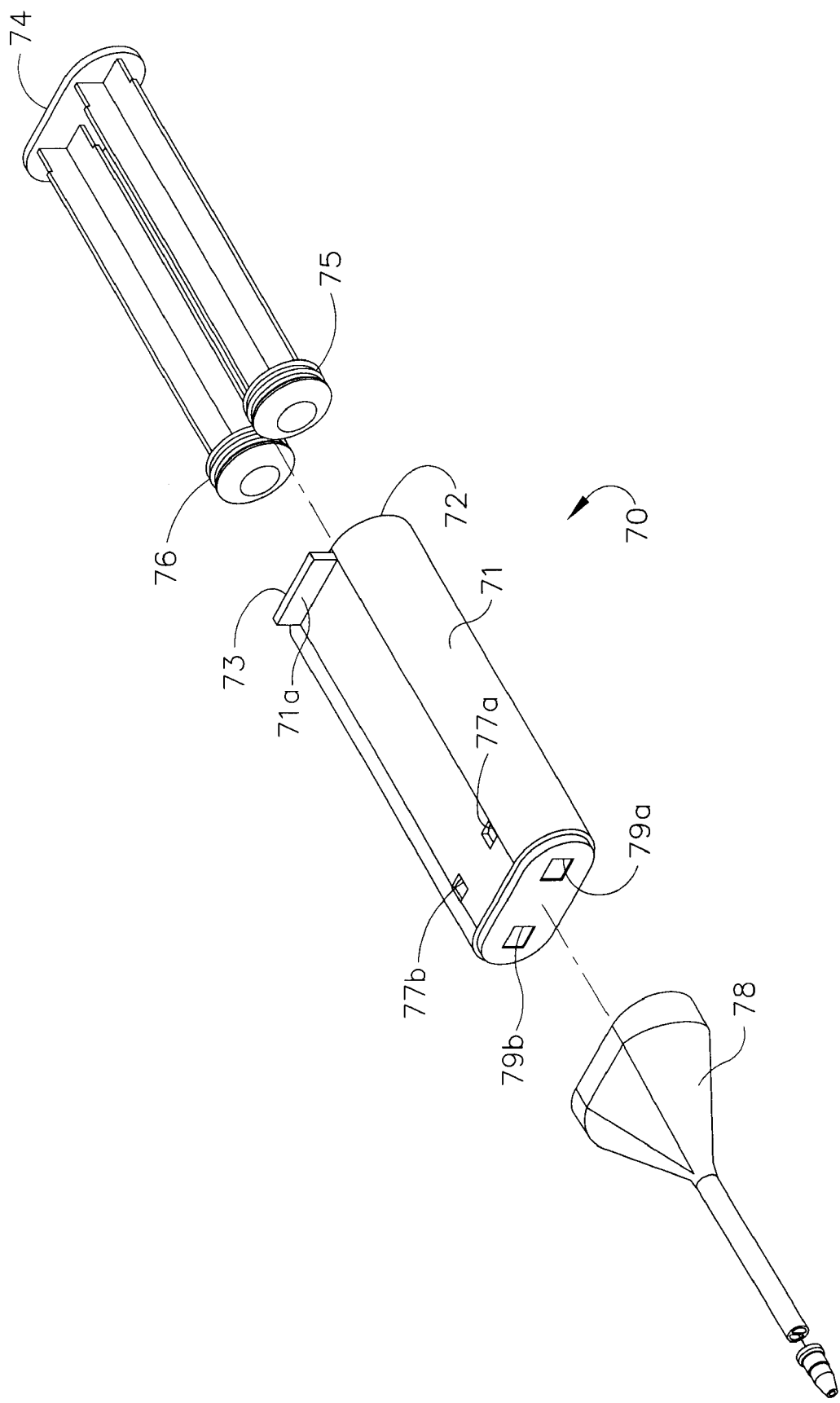
FIG. 4 is an exploded isometric view of the replaceable empty cartridge of FIG. 3.
Figure 5:
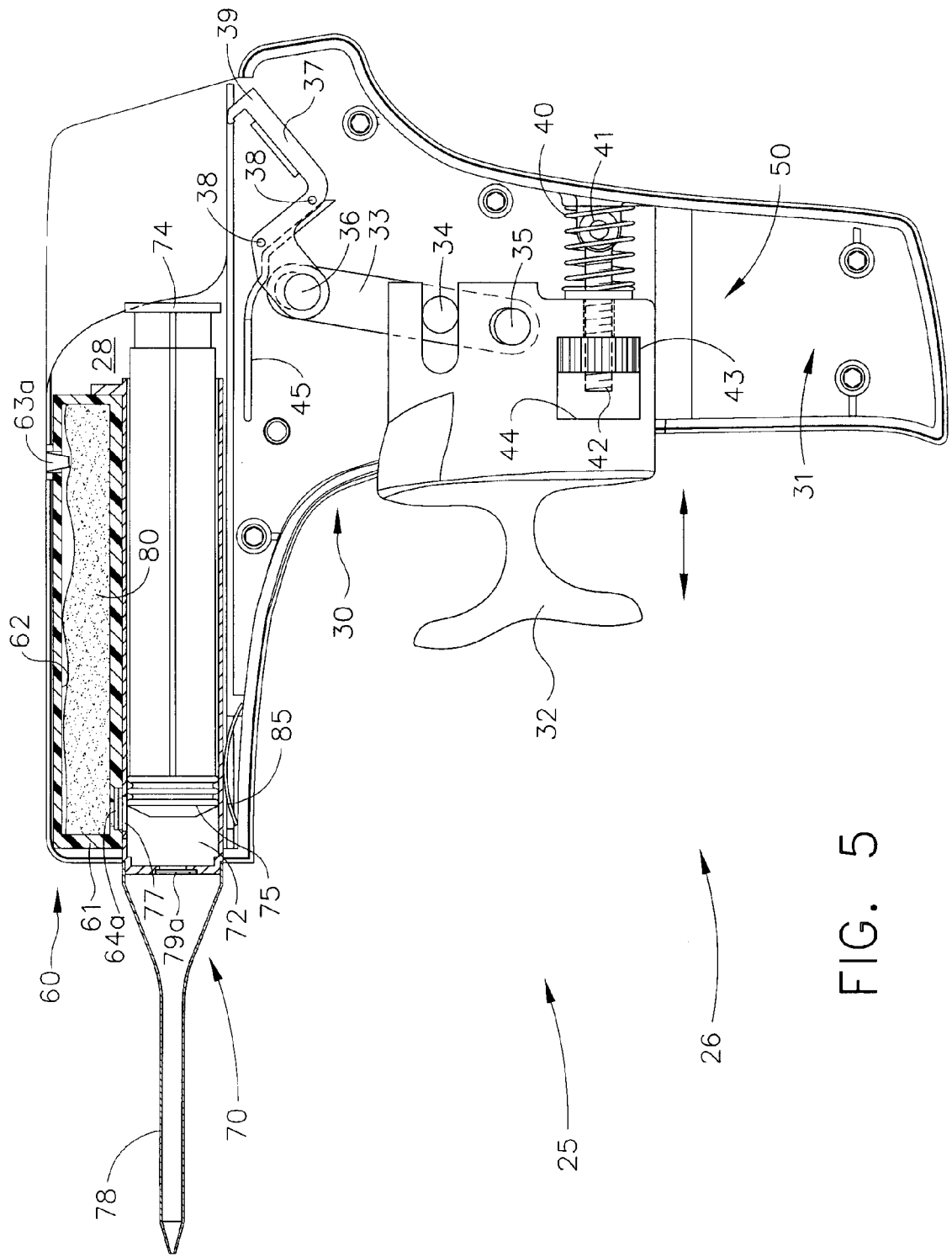
FIG. 5 is a cross sectional side view of the adhesive dispensing device showing the actuator handle of FIG. 1 combined with the empty cartridge of FIG. 4.

FIGS. 1-8 can show a first embodiment of an adhesive dispensing device 25 that combines an actuator handle 26 that contains a two part adhesive with a replaceable empty cartridge 70 (FIG. 5). The adhesive dispensing device 25 can store the adhesive components in the actuator handle 26 and a first actuation of the adhesive dispensing device 25 can draw the adhesive components from chambers in the actuator handle 26 and into chambers of replaceable empty cartridge 70. A second actuation of the adhesive dispensing device 25 can mix and dispense the adhesive components drawn into the empty cartridge 70. A third actuation can draw additional adhesive components from chambers in the actuator handle 26 and into the newly emptied chambers of replaceable empty cartridge 70. A fourth actuation mixes and dispenses the second draw of adhesive components. Should the adhesive firings block the replaceable empty cartridge 70 in the adhesive dispensing device 25, the first replaceable empty cartridge 70 can be replaced with a second fresh empty replaceable empty cartridge 70. Alternately, the surgeon may elect to store the adhesive dispensing device 25 and can remove the replaceable empty cartridge 70 for storage.

Figure 1:
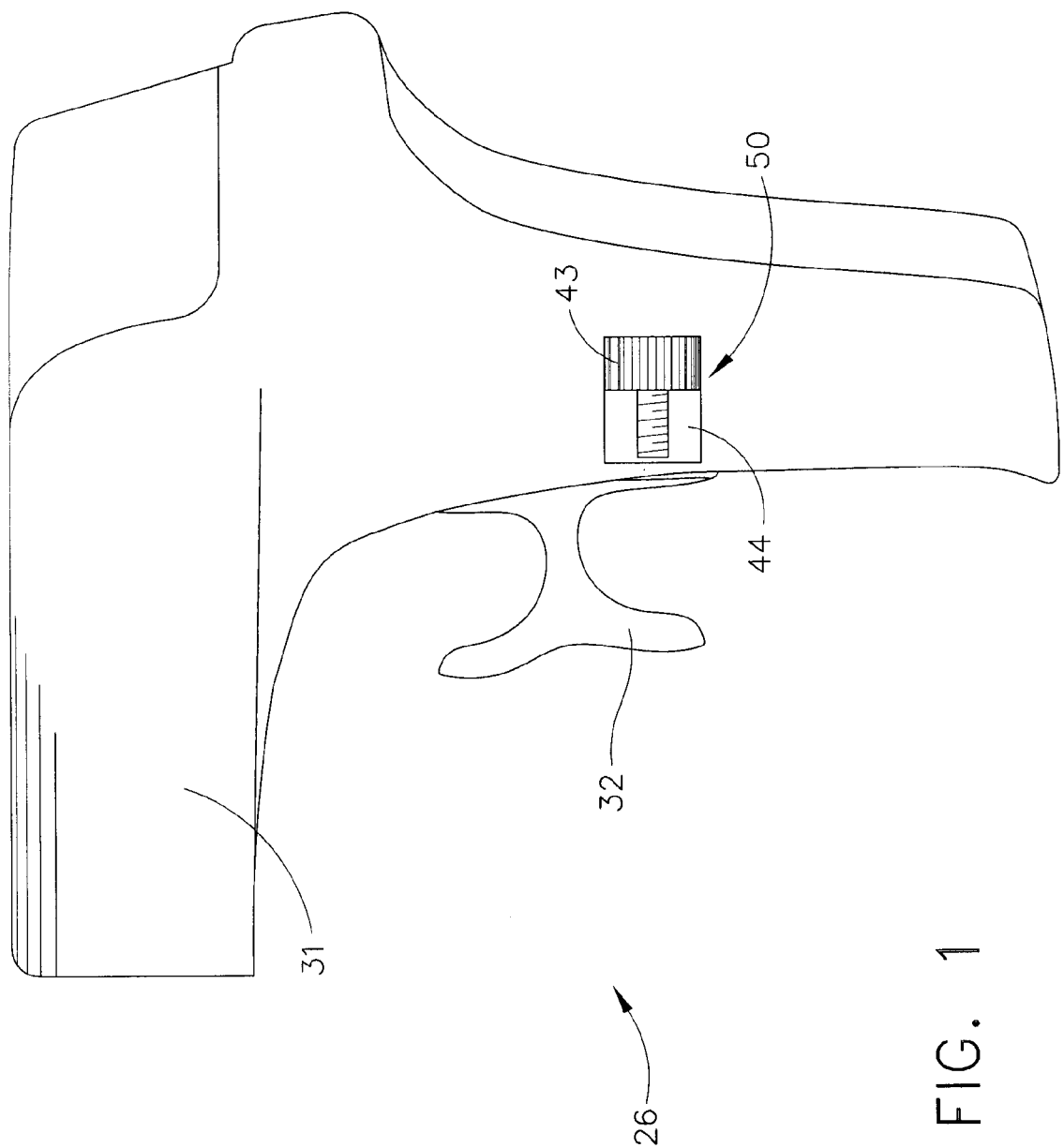
FIG. 1 is a side view of an actuator handle of an adhesive dispensing device containing a first and a second part of an adhesive.
Figure 2:
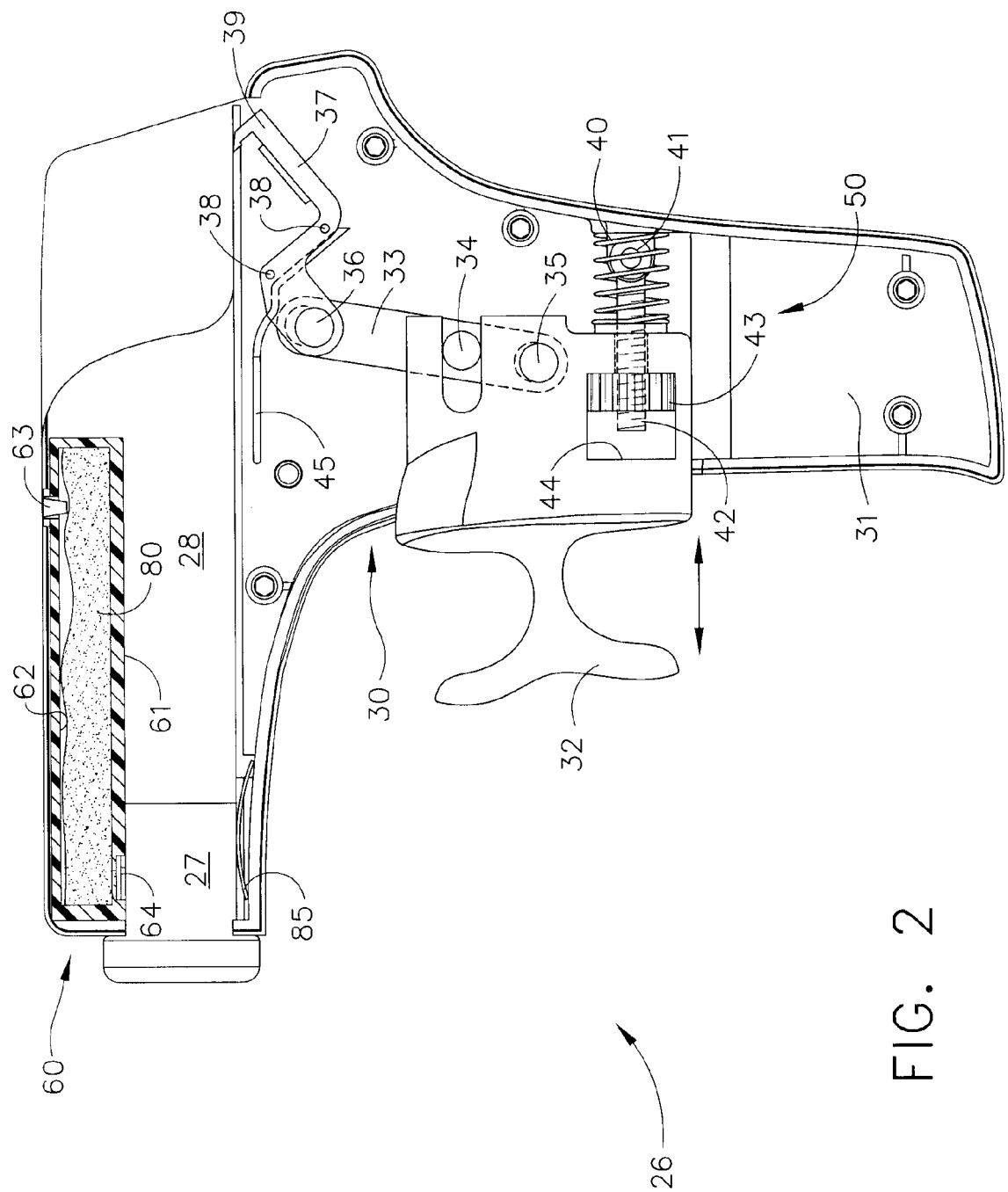
FIG. 2 is a cross sectional side view of an actuator handle of FIG. 1 showing an adhesive dispensing device containing a first and a second adhesive component of an polymer adhesive.

FIGS. 1-2 show the elements of the actuator handle 26. Actuator handle 26 comprises, a firing mechanism 30 to dispense the adhesive, a handle body 31 to grip, a volume control mechanism 50 to control the volume of adhesive dispensed, and an adhesive cartridge 60 to contain the adhesive. In FIG. 2 one half of the handle body 31 has been removed to show the elements of the actuator handle 30, and a shipping plug 27 is located in a cartridge opening 28 within the actuator handle 26. A cartridge spring 85 pushes upwardly on shipping plug 27.

As shown, a firing trigger 32 can move proximally and distally within actuator handle 26 in response to actuation and de-actuation of the firing trigger 32. A spring 40 can be provided to return trigger 32 to the un-actuated position. A trigger link 33 may have a trigger pin 35 rotatably mounted within the trigger 32 and pivoting about a boss 34 in response to actuation and de-actuation of the trigger 32. A cartridge link 37 may pivotally mount on a cartridge pin 36 of the trigger link 33. Cartridge link 37 can have cam pins 38 extending into and out of cartridge link 37 that engage with and are guided by a cam plate 45 extending inwardly from each half of the handle body 31. A syringe cup 39 can extend from the cartridge link 37 to operably engage with the replaceable empty cartridge 70

The volume control mechanism 50 can control the volume of the adhesive dispensed by controlling the stroke of the firing trigger 32. Firing trigger 32 may slide within actuator handle 30 and engage with spring 40. Volume control mechanism could have a volume boss 41 extending from the handle 31 and a threaded screw arm 42 that pivotally mounts to the boss 41 and slides within firing trigger 32. A knurled knob 43 may be threaded onto threaded screw arm 42 in a window 44 in firing trigger 32 to compress spring 40. The stroke of the firing trigger 32 may be limited to the travel of the knurled knob 43 in the window 44. Rotation of the knurled knob 43 moves the firing trigger relative to the handle body 31, changes the angle of the trigger link 33 and the position of the cartridge link 37 on the cam plate 45, and controls the stroke of the cartridge link 37 when the syringe cup 39 is engaged with the replaceable empty cartridge 70.

The adhesive cartridge 60 could be located above the cartridge opening 28 and is shown in a cross section across one of two adhesive reservoirs. Cartridge 60 may have a shell 61 containing two adhesive reservoirs such as first reservoir 62 and second reservoir 65. A first adhesive fill valve 63a and a second adhesive fill valve 63b can be located in the top of the first reservoir 62 and the second reservoir 63 respectively. The adhesive fill valves 63a, 63b can double as a pressure valves in the top of the cartridge 60 to draw air in as adhesive is withdrawn. A normally closed first adhesive exit valve 64a and a normally closed second adhesive exit valve 64b could operably connect with the first reservoir 62 and the second reservoir 63 respectively and can be located in the bottom of the cartridge 60. Valves 64a, 64b can be formed from elastomer materials and may be kept closed during shipping by a shipping plug 27. A first adhesive component 80 can be located in first reservoir 62 and a second adhesive component 81 can be located in the second reservoir 65.

FIGS. 3 and 4 can show the replaceable empty cartridge 70 that can be used with actuator handle 26. Empty cartridge 70 can have a body 71 containing an empty first chamber 72 and an empty second chamber 73 and an insertion stop 71a on a proximal end of the body 71. A dual plunger 74 could be slidably received within a body 71 and have a first piston 75 that is slidably received in empty first chamber 72 and a second piston 76 that is slidably received in empty second chamber 73. A pair of loading openings 77a and 77b can operably engage with empty first chamber 72 and empty second chamber 73 respectively. A one way flapper valve such as first exit valve 79a can be located at a distal end of the first chamber 72 and swing closed when a draw is placed on first chamber 72 and swing open in response to pressure from the first chamber 72. A second exit valve 79b can also be located at a distal end of the second chamber 73 to swing closed when a draw is placed on second chamber 73 and to swing open in response to pressure from the second chamber 73. A nozzle 78 can be permanently attached or removably attached to the end of the body 71.

FIGS. 5 to 10 can show the operation of the adhesive dispensing device 25. In FIG. 5, the shipping plug 27 is removed from the cartridge opening 28 and the replaceable empty cartridge 70 is installed in the actuator handle 26. Replaceable empty cartridge 70 is shown sectioned across empty first chamber 72. Cartridge spring 85 can push upwardly on replaceable empty cartridge 70 to ensure that the loading openings 77a, 77b connected to the empty first and second chambers 72, 73 are pushed against the first and second adhesive exit valves 64a, 64b to create a seal. The trigger 32 has not been actuated to bring syringe cup 39 into engagement with the dual plunger 74.

Figure 6:
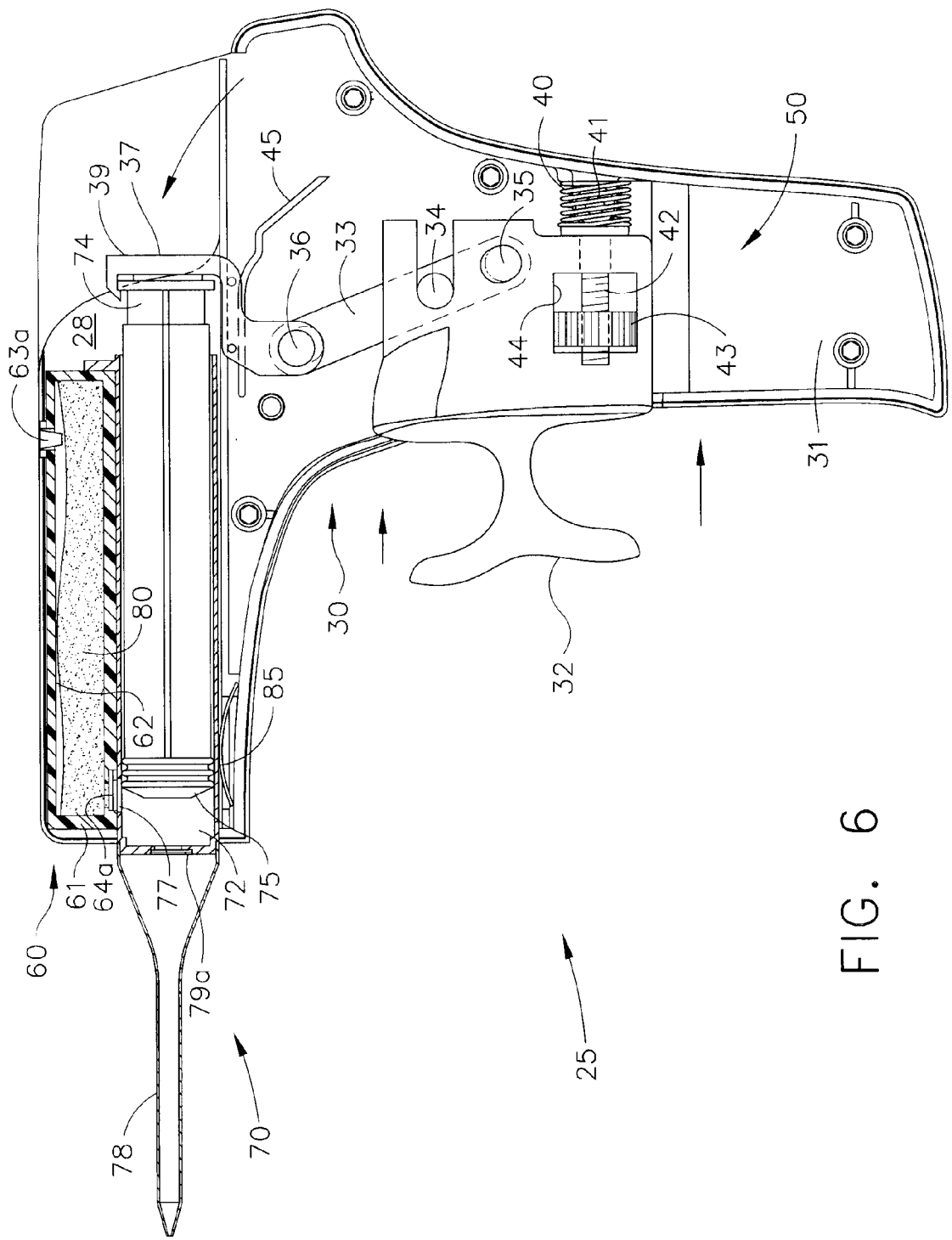
FIG. 6 is a cross sectional side view of FIG. 5 showing a first movement of the elements of the adhesive dispensing device from an initial actuation of a firing trigger to purge air from the replaceable empty cartridge.

In FIG. 6, the firing trigger 32 could have been actuated to pivot trigger link 33 on boss 34, and to guide the cartridge link and attached syringe cup 39 along the cam plate 45 into engagement with the dual plunger 74 and to purge air from the empty cartridge 70. If required, the surgeon can exert force in the distal direction on the syringe cup 39 to ensure locked engagement with the dual plunger 74.

Figure 7:
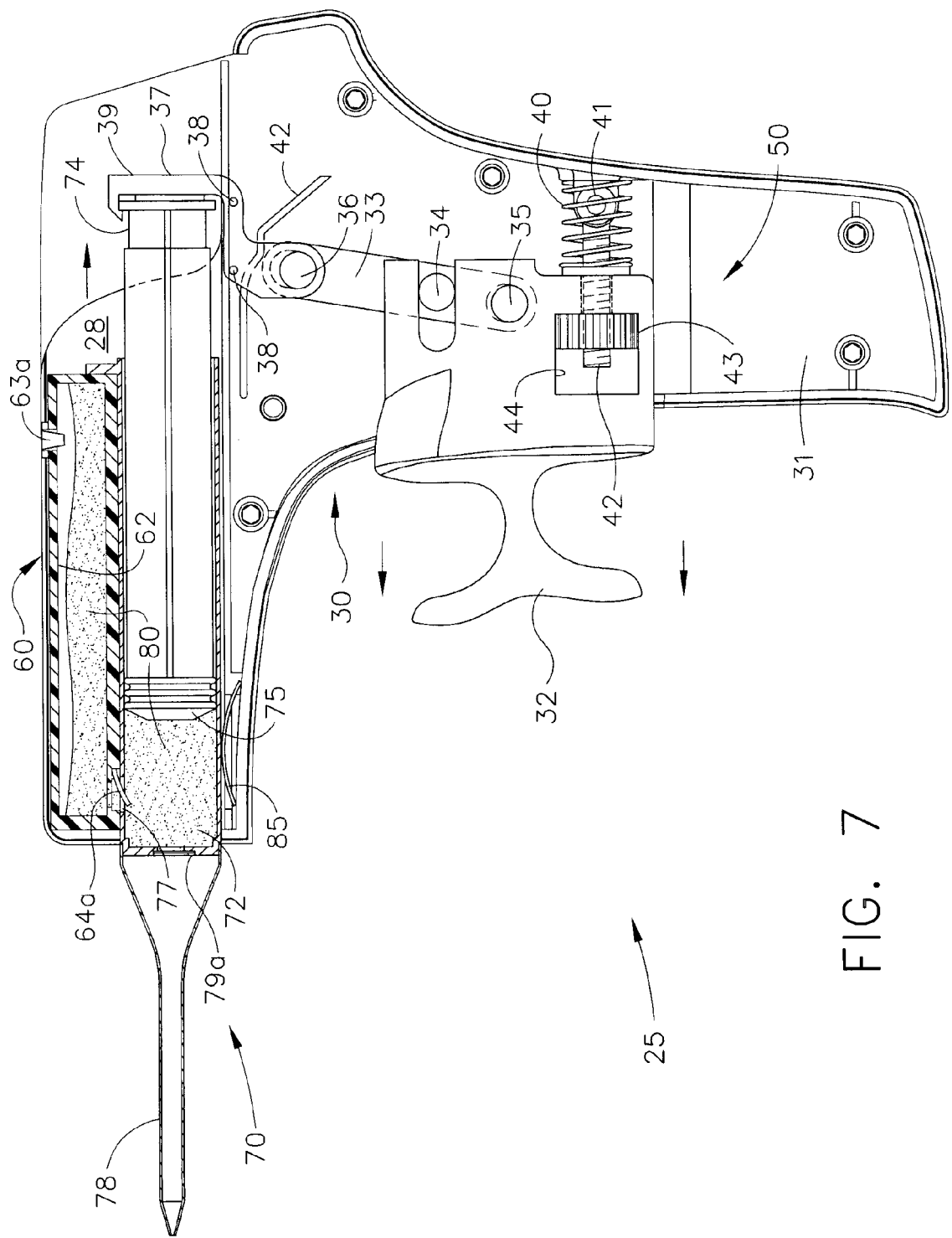
FIG. 7 is a cross sectional side view of FIG. 6 showing a second movement of the elements of the adhesive dispensing device from releasing the firing trigger to draw the adhesive components into the replaceable empty cartridge.

In FIG. 7, the trigger 32 can be released and the spring 40 can return trigger 32 and the pivot trigger link 33 back to the position of FIG. 5. The syringe cup 39 may be pulled proximally by the pivot trigger link 33 to draw the dual plunger 74 of the replaceable empty cartridge 70 proximally. Proximal motion of the dual plunger 74 can close first and second exit valves 79a, 79b, and draw first and second adhesive components 80, 81 from the first and second reservoirs 62,63, through the open adhesive exit valves 64a and 64b, into loading opening 77a, 77b, and into empty first and second chambers 72, 73 respectively. A second stroke of the trigger 32 moves syringe cup 39 and dual plunger 74 distally to pressurize the first and second chambers 72, 73 filled with adhesive components 80, 81 and close the adhesive fill valves 63a, 63b and opens the adhesive exit valves 64a, 64b. This action forces the adhesive components from the first and second chambers 72, 73 into the nozzle 78 to be mixed, and applies the mixed adhesive components 80, 81 to tissue. A third stroke of the firing trigger 32 refills the replaceable empty cartridge 70 with fresh adhesive components 80, 81 from the adhesive cartridge 60 and a fourth stroke dispenses the mixed adhesive onto tissue.

Figure 8:
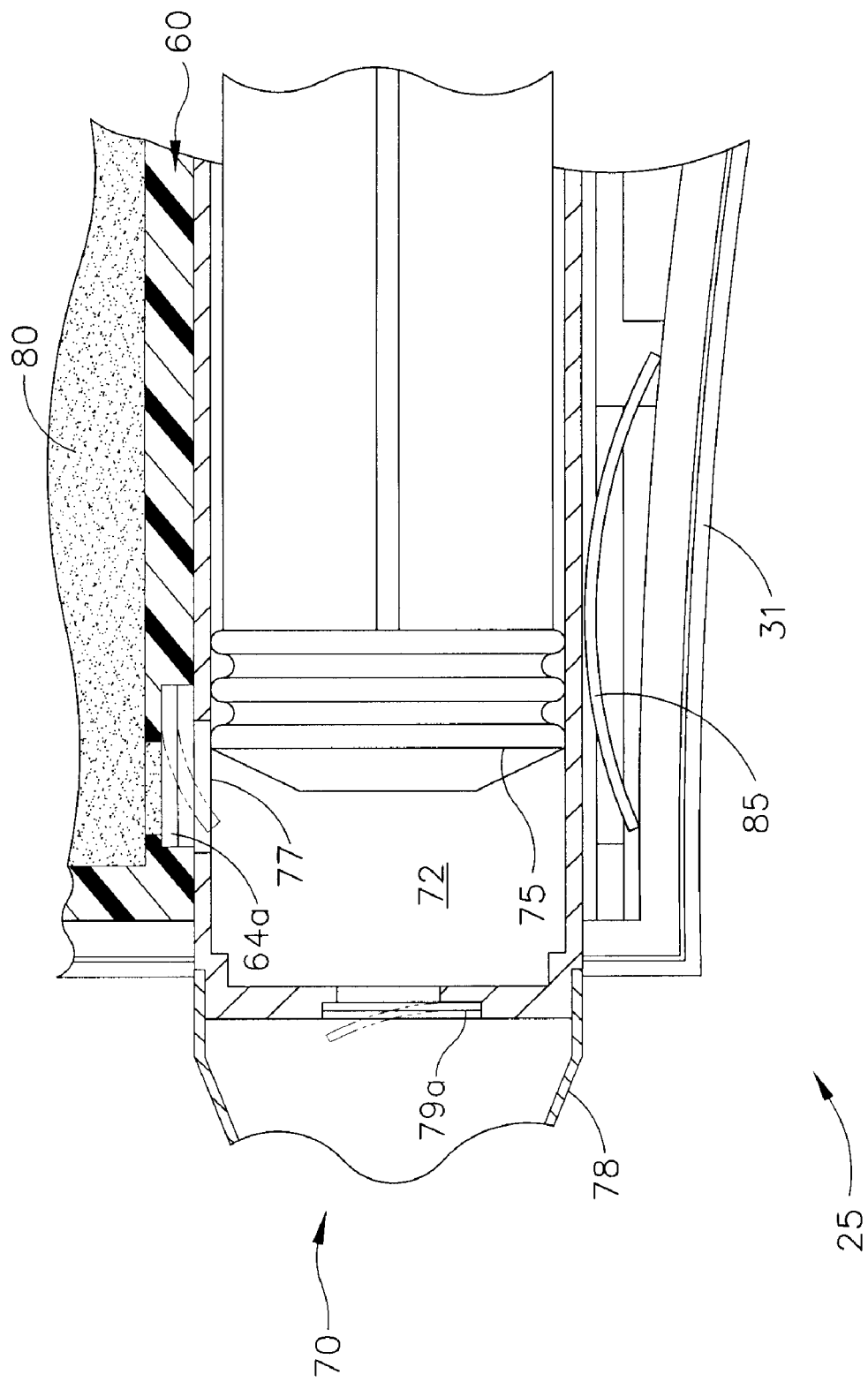
FIG. 8 is a cross sectional side view of FIG. 5 showing a pair of flapper doors within the adhesive dispensing device used to control adhesive component movement therethrough.

FIG. 8 is a partial cross sectional of the view of the replaceable empty cartridge 70 sectioned across empty first chamber 72 and in actuator handle 26. The view shows a flapper door of the elastomeric adhesive exit valve 64a, and how the flapper door can open in response to a draw in first chamber 72, and can close in response to pressure in first chamber 72. Spring 85 forces the empty cartridge 70 upwards to engage with and seal with elastomeric adhesive exit valve 64a and 64b. Also by way of example, the flapper doors could be metallic springs or elastomeric materials. The flapper door of the first exit valve 79a is also shown, and how the flapper door can close in response to a draw in first chamber 72, and can open in response to pressure in first chamber 72. Spring 85 forces the empty cartridge 70 upwards to engage with and seal with elastomeric adhesive exit valve 64a and 64b.

Alternate Replaceable Cartridge

Figure 9:
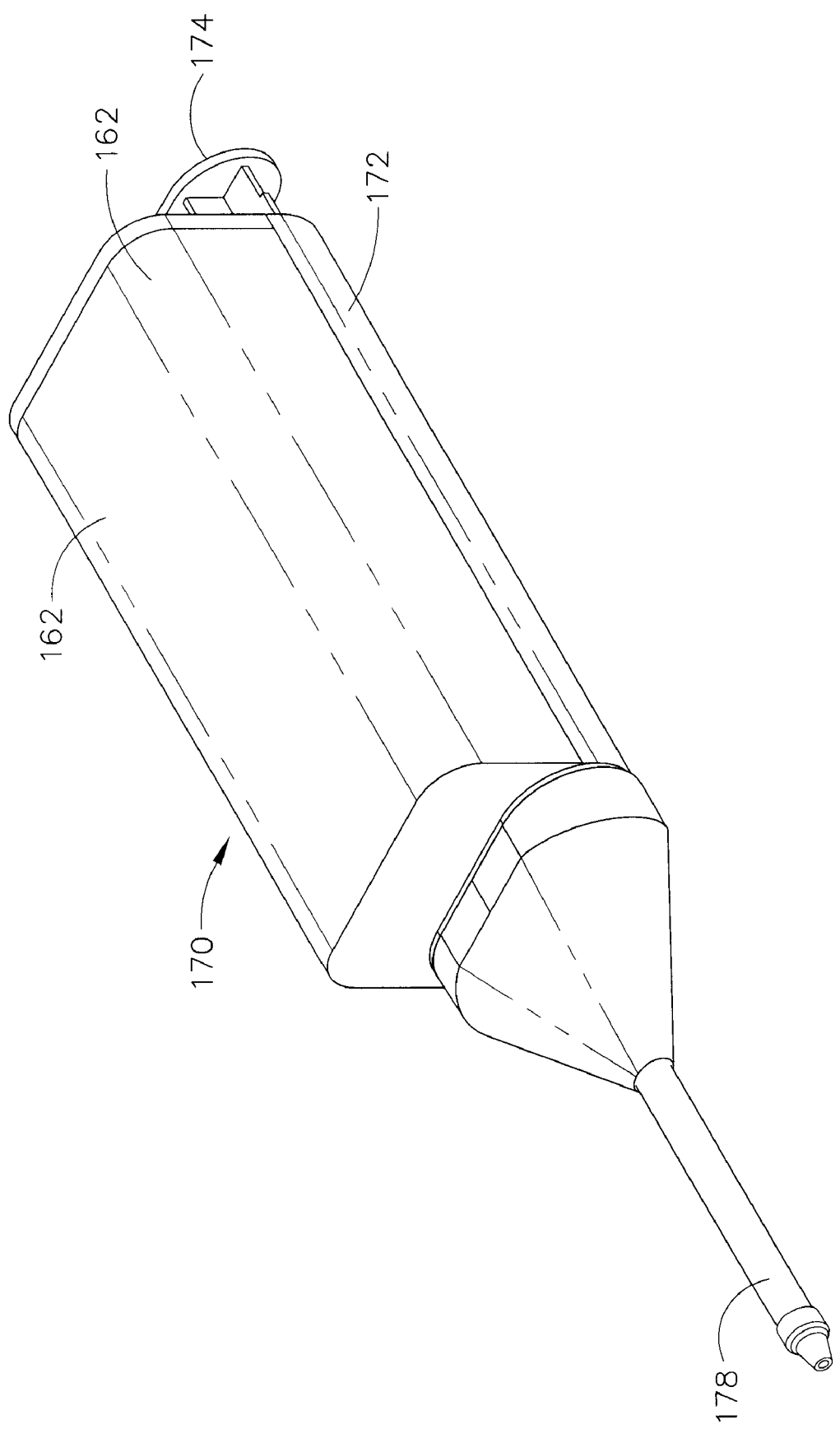
FIG. 9 is a cross sectional side view of an alternate replaceable cartridge containing a first and a second adhesive component and having a third and a fourth empty chamber therein.
Figure 10:
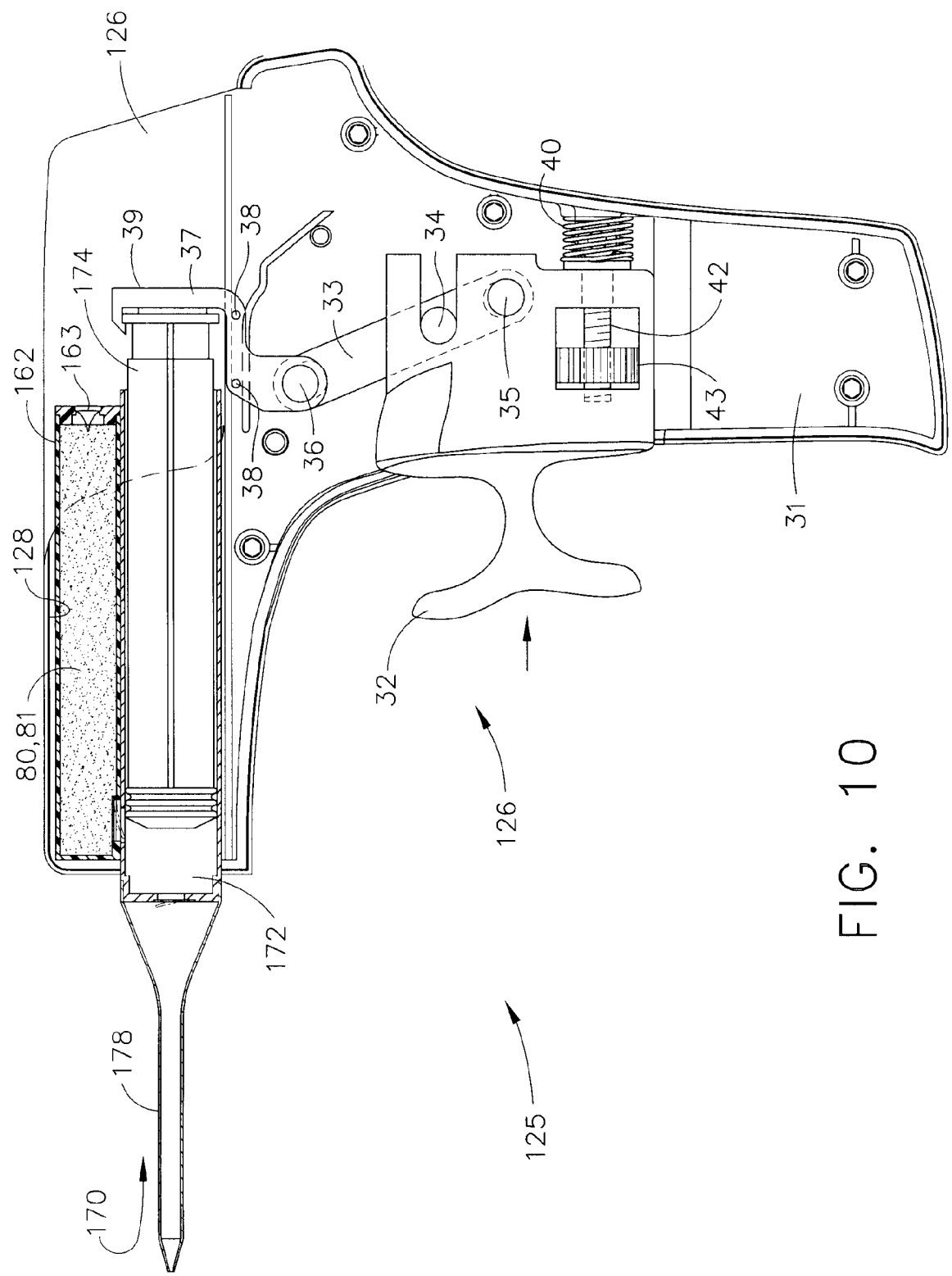
FIG. 10 is a side view of an alternate actuator handle of an alternate adhesive dispensing device assembled with the alternate replaceable cartridge of FIG. 9.

FIGS. 9 and 10 can show an alternate embodiment of a replaceable cartridge such as alternate cartridge 170 that can be used with an alternate embodiment of the actuator handle 126 in an alternate dispensing device 125. The alternate cartridge 170 embodiment is a single replaceable cartridge that is a combination of the replaceable empty cartridge 70 described previously with the adhesive cartridge 60. The alternate cartridge 170 can have a pair of first chambers 162 filled with separate adhesive components 80, 81 and a pair of empty chambers 172 that can draw the adhesive components 80, 81 with a dual plunger 174 from the first pair of chambers 162 and dispense them from a nozzle 178 of the alternate cartridge 170 multiple times. Should the alternate cartridge 170 become blocked, the entire alternate cartridge 170 and adhesive components 80, 81 can be discarded FIG. 10 shows a cross sectional side view of the alternate cartridge 170 installed on the alternate actuator handle 126. Alternate cartridge 170 is shown in cross section locked into opening 128 of the alternate actuator handle 126. The first pair of adhesive filled chambers 162 are attached to the second pair of empty chambers 172 and the dual plunger 174 is operatively coupled to the firing trigger 32 by syringe cup 39. Operation is one pull of firing trigger 32 to load the empty chambers 172 with adhesive components and a second pull to dispense and mix the adhesive components from the alternate cartridge 170. A pair of adhesive fill valves 163 can be provided to refill the first pair of adhesive filled chambers 162.

Adhesive Mixing Device with Gas Assisted Mixing

FIGS. 11-17 can show another alternate embodiment of an adhesive dispensing device 225 that combines a gas assisted mixer system 200 to pressurize, mix and dispense the adhesive components 80, 81 from a pair of adhesive chambers 262 within a gas actuator handle 226 that feed a pair of empty chambers 272 within an empty replaceable gas cartridge 270. Once again, a first actuation of a firing trigger 232 draws adhesive from adhesive chambers within a gas actuator handle 226 and feeds the adhesive into the pair of empty chambers of replaceable gas cartridge 270. A second actuation of firing trigger 232 dispenses the adhesive components 80, 81 from chambers 272 and from a nozzle 278 of the gas cartridge 270. Alternately, actuation of a gas trigger 205 in lieu of the second actuation of firing trigger 232 simultaneously dispenses the adhesive components 80, 81 from chambers 272 and feeds gas from the gas actuator handle 226 and into the replaceable gas cartridge 270. The gas mixes with the adhesive elements 80, 81 within nozzle 278 of the empty replaceable gas cartridge 270 and ejects the mixed adhesive therefrom.

The adhesive dispensing device 225 can have the previously described pair of first adhesive chambers 262 within the gas actuator handle 226 that are filled with separate adhesive components 80, 81. The first adhesive chambers 262 feed adhesive components 80, 81 into a pair of empty chambers 272 within the replaceable gas cartridge 270 with a first actuation of a firing mechanism 230 and dispense adhesive components 80, 81 with a second actuation. Firing mechanism 230 can be located within the actuator handle 226 and may use many of the previously described elements to draw adhesive components 80, 81 from the pair of first adhesive chambers 262 into the a pair of empty chambers 272 with the first actuation and dispense them with a second actuation.

The gas assisted mixer system 200 can have a pressure bottle 201 containing a high pressure gas 202 sealed therein. A rotatable needle valve 203 can be provided that can breach a seal 204 of the pressure bottle 201 to pressurize the gas assisted mixer system 200 with gas 202. Once seal 204 is breached, the gas 202 travels upwards to a sealed actuation valve 205 (see FIGS. 11-13). Actuation valve 205 has a seal 206 that is normally sealed until breached by a pin 207 upon first activation of the trigger 232 (FIGS. 12 and 13). Once seal 206 is breached, gas 202 flows to and is stopped at gas trigger 208. Gas trigger 208 opens to pass gas 202 upon actuation and closes on de-actuation. A gas line 209 extends from gas trigger 208 to a gas seal 210 that operably seals with an opening 267 in a gas channel 266 in the replaceable gas cartridge 270. Thus, once the rotatable needle valve 203 is actuated, and after the firing trigger 232 has been activated a first time to breach seal 206 and to load adhesive components 80, 81 into a pair of empty chambers 272, the adhesive dispensing device 225 is ready to dispense adhesive components 80, 81. Note that gas trigger 208 can be mounted on firing trigger 232 and that actuation of gas trigger 208 can simultaneously actuate or move firing trigger 232 to dispense adhesive components 80, 81 along with the gas 202 from a nozzle 178 of the alternate cartridge 170, which is depicted in FIGS. 9-10.

Figure 17:
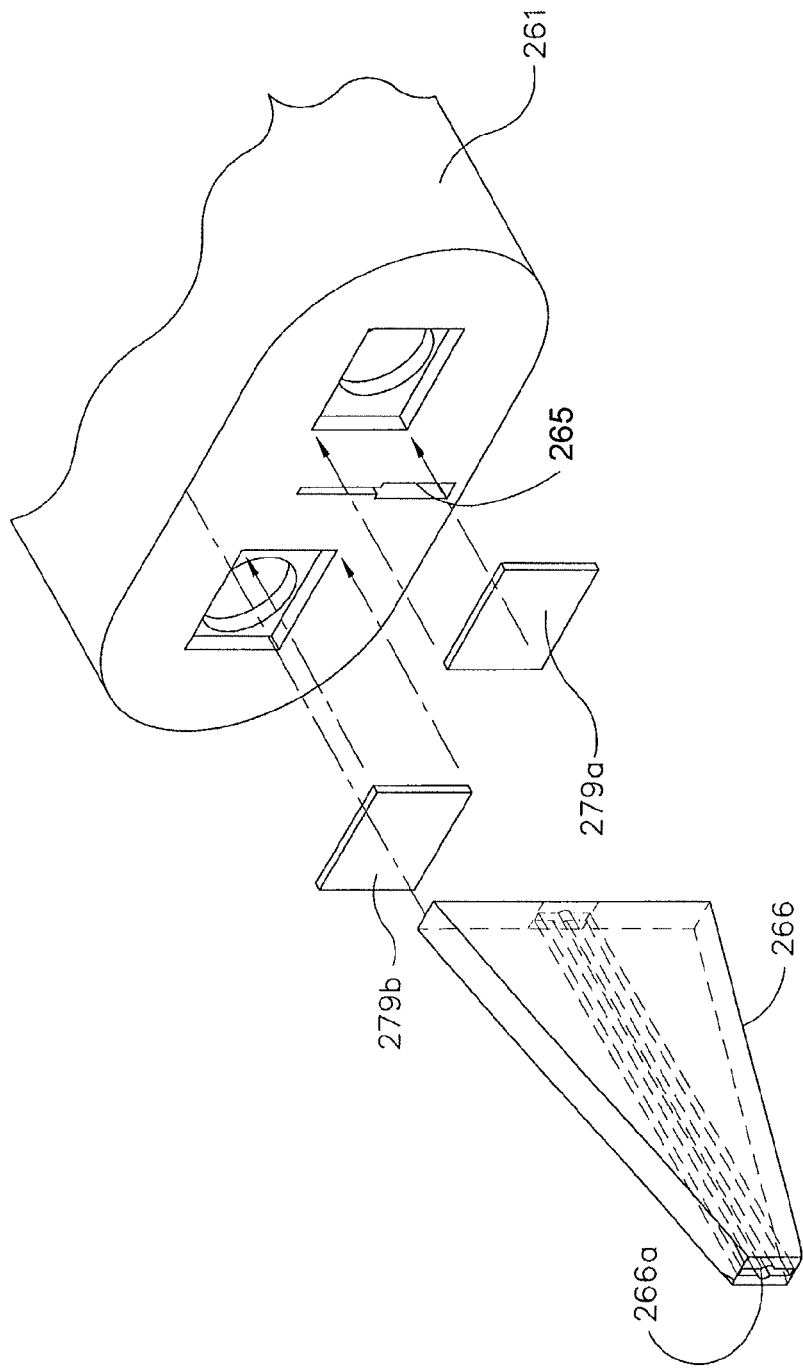
FIG. 17 is an isometric exploded view of a pair of flapper doors and a gas dispersement guide of the empty gas assist cartridge of FIG. 15.

FIGS. 14-17 can show the elements of an empty replaceable gas cartridge 270 that can be used with the gas actuator handle 226 and the gas assisted mixer system 200 to pressurize, mix, and dispense the adhesive components 80,81 from the replaceable gas cartridge 270. FIG. 14 shows a cross section of a cartridge body 261 showing the pair of empty chambers 272 for the adhesive components 80,81 and the gas channel 265 with the opening 267 therein. FIG. 15 can be an exploded view of gas cartridge 270 showing dual plunger 274 insertable in the pair of empty chambers 272 therein. A pair of exit valves 279a and 279b are flapper valves that seal empty chambers 272 upon draw and open upon actuation of the firing trigger 232. Nozzle 278 has a funnel 290 that attaches to a distal end of cartridge body 261 and a shaft 291 extending distally from funnel 290. Shaft 291 has a first component passage 291a and a central gas passage 291b and a second component passage 291c extending longitudinally therethrough. A divider 266 mounts within funnel 290 and separates adhesive components in funnel 290. A gas channel 266a extends through divider 266 and when nozzle 278 and divider 266 are attached together, couples the gas channel 265 of the body 261 with the central gas passage 291b of the shaft. A mixer 293 and tip 294 attach to a distal end of shaft 291 to mix the gas and adhesive together as it is ejected from the tip 294. FIG. 17 is an enlarged view of a distal end of the cartridge body 271 and the divider.

Alternately, in another embodiment of the gas assisted mixing system (not shown), the gas source can be an air line or gas line from the operating room operably coupled to the gas trigger 208.

Alternate Rotating Blade Mixer Embodiment

FIGS. 18-20 illustrate a first embodiment of a rotating mixer tip 425 that can work with hand pumped adhesive components 80, 81 and with gas assisted mixing described above. The rotating mixer tip 425 can attach to a distal end of the shaft 291 and can comprise a rotating mixer blade 426 that rotatably mounts on a shaft 427 extending from shaft block 428. A blade lock 429 attaches to a distal end of shaft 427 to capture rotatable mixer blade 426 thereon. The assembly of shaft block 428, shaft 427, rotating mixer blade 426 and blade lock 429 fits into a slot 430 in mixer tip 431. A divider blade 432 is provided to divide adhesive components 80, 81 until they enter rotatable mixer blade 426. Gas assist can pass gas about one side or the other of divider blade 432 to spin mixer blade 426.

Alternate Spiral Mixer Embodiment

Figure 21:
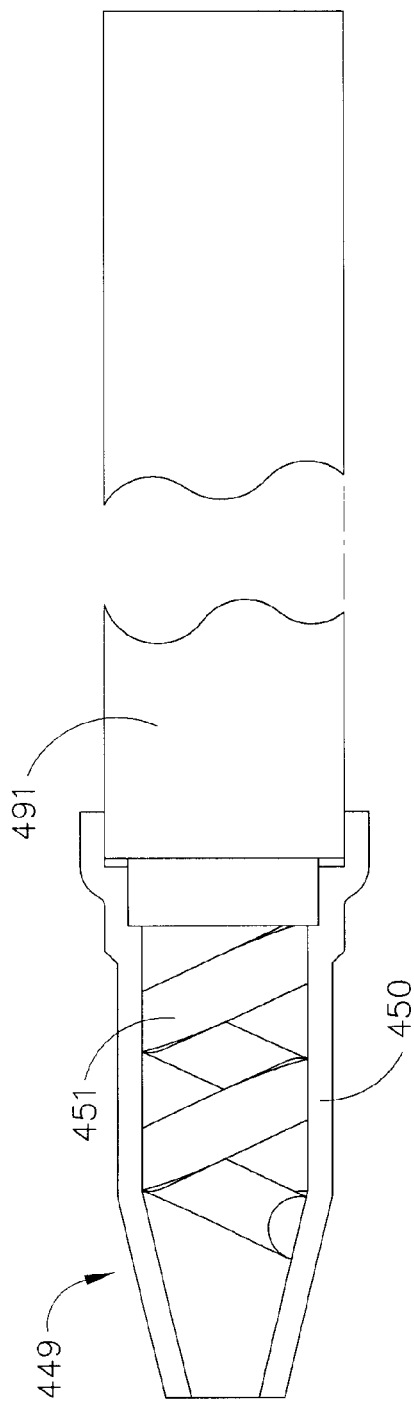
FIG. 21 is a cross sectional view of a second alternate nozzle suitable for any alternate embodiments above having a spiral mixer blade to mix the adhesive components.
Figure 23:
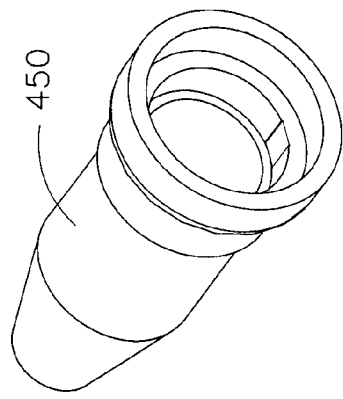
FIG. 23 is an isometric view into an end piece of the alternate nozzle of FIG. 21.
Figure 22:
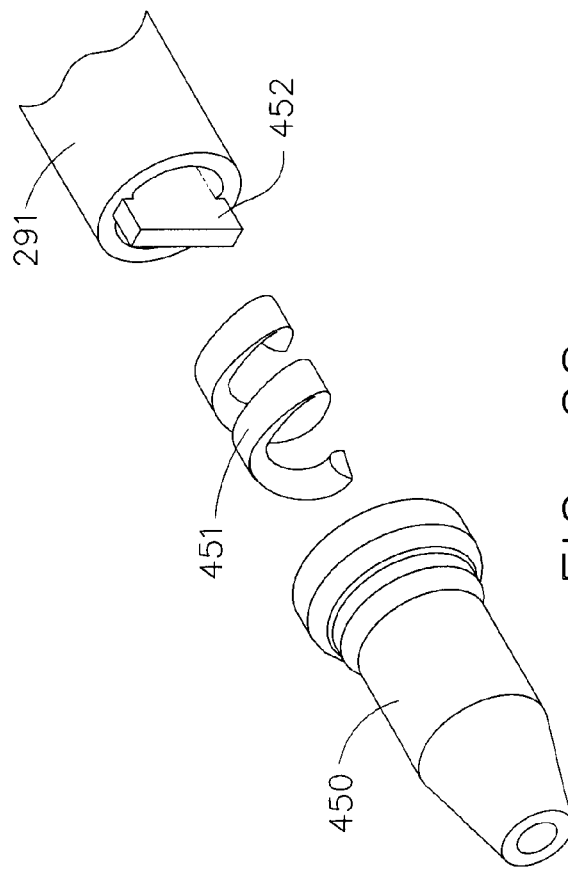
FIG. 22 is an isometric exploded view of the second alternate nozzle of FIG. 21 showing the spiral mixer blade.

FIGS. 21-23 illustrate a second embodiment of a mixer tip such as spiral mixer tip 449 that can work with hand pumped adhesive components 80, 81 and with gas assisted mixing described above. The spiral mixer tip 449 can attach to a distal end of the shaft 491 and can comprise a nozzle 450 that contains a spiral 451 therein. A divider blade 452 is provided to divide adhesive components 80, 81 until they enter spiral 451 which twists and mixes adhesive components 80, 281 as they pass therethrough.

Multi Channel Adhesive Dispensing Device

As described above, clogged nozzles frequently force surgeons to dispose of adhesive dispensing devices. As shown in FIGS. 24-34 one example of a solution is an adhesive dispensing device 325 that can comprise an adhesive handle 326 containing one or more adhesive components and a pump, and a rotatable indexing nozzle 350 containing a plurality of open passageways and tips that can conduct adhesive from the adhesive gun 326, through a first passageway and out of a first tip and onto tissue. Should the first tip become clogged or blocked with adhesive, a second passageway and second tip can be rotated into alignment with the adhesive outlet or outlets of the adhesive gun 326. This rotation can provide a fresh path for the adhesive components to flow from the adhesive gun 326 onto tissue.

Figure 24:
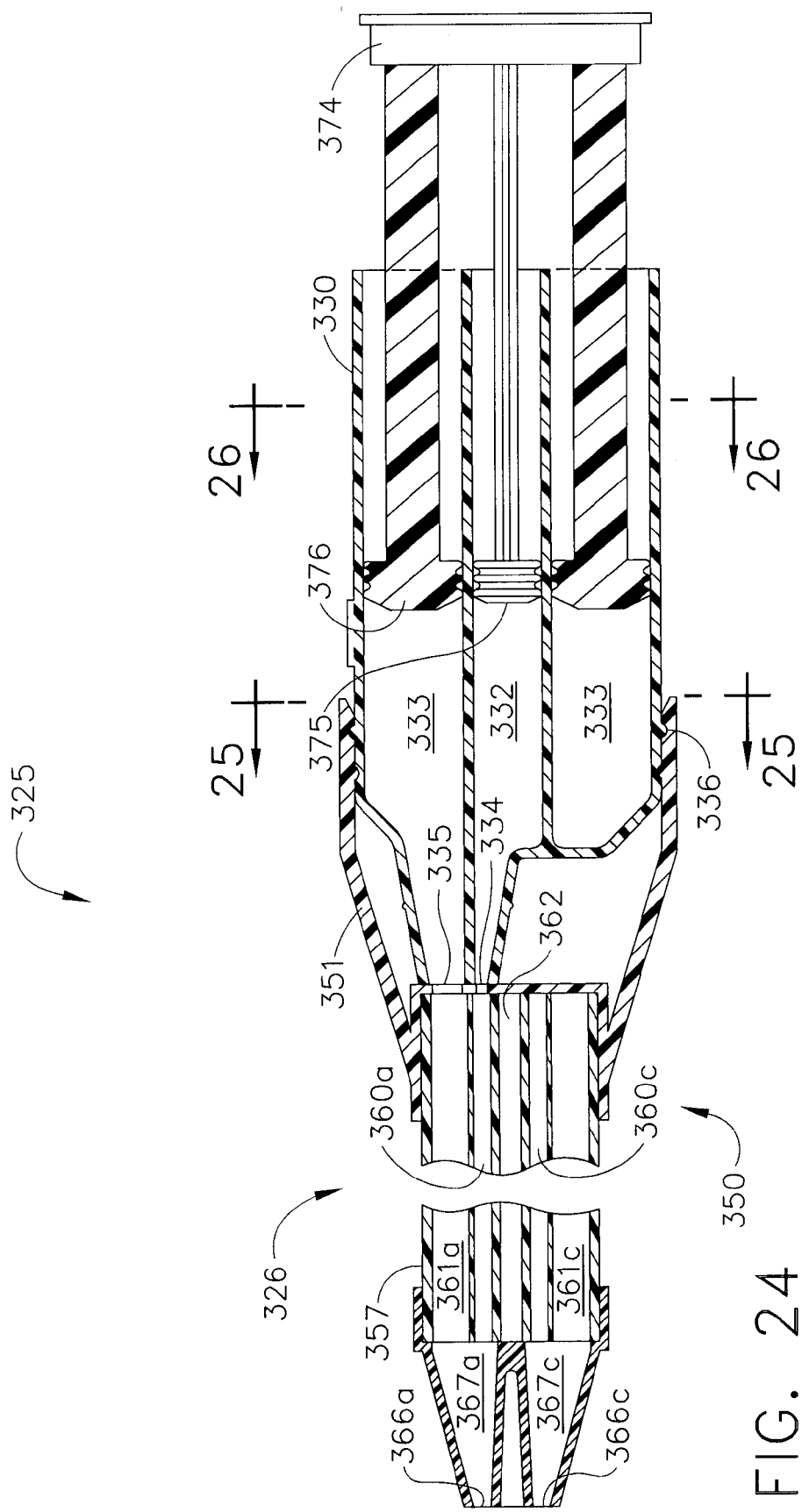
FIG. 24 is a side cross sectional view of an alternate adhesive dispensing device having a handle with two chambers of adhesive components and a pump therein, and a rotary nozzle containing a plurality of orifices that mix and apply the adhesive components onto tissue.
Figure 26:
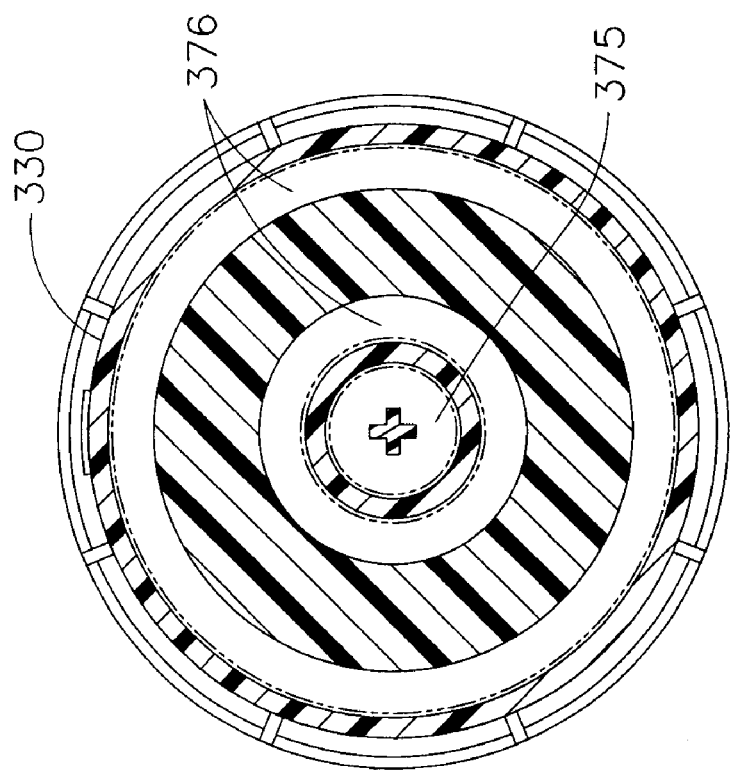
FIG. 26 is an end cross sectional view of the alternate adhesive dispensing device of FIG. 24 across a circular and a donut shaped plunger of the pump.
Figure 25:
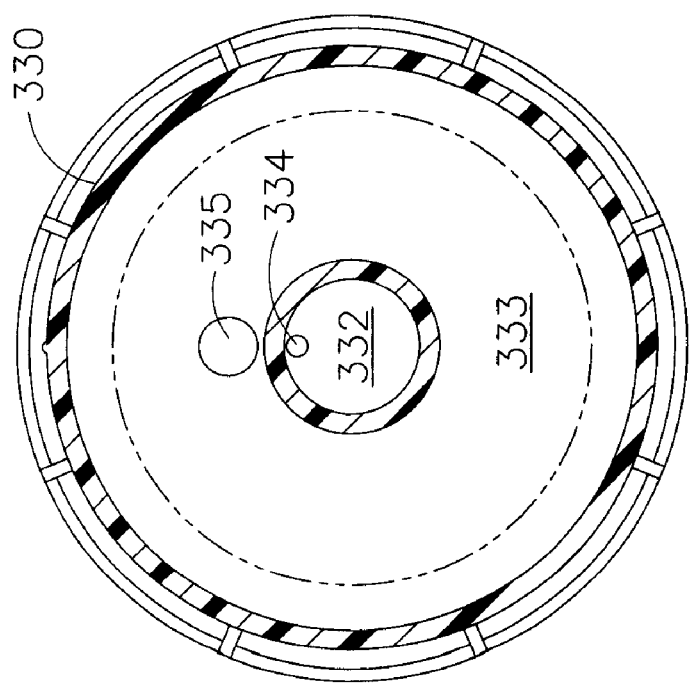
FIG. 25 is an end cross sectional view of the alternate adhesive dispensing device of FIG. 24 showing a circular shaped chamber and a donut shaped chamber to contain the first and the second adhesive components therein.

FIGS. 24-26 are cross sectional view of an adhesive dispensing device 325 with the adhesive handle 326 and the indexing nozzle 350 rotatably attached. Adhesive handle 325 has a cylindrical body 330 with a small cylindrical inner chamber 332 filled with the first adhesive component 80 surrounded by a ring shaped second outer chamber 333 filled with the second adhesive component 81. A plunger 374 has a circular piston 375 that slidably mounts within circular inner chamber 332 and a second ring plunger 376 that slidably mounts within ring shaped outer chamber 333. As best shown in FIG. 25, the circular inner chamber 332 has a first bore 334 at a distal end of the chamber for passage of the first adhesive component 80 therethrough. The ring shaped outer chamber 333 has a second bore 335 at a distal end of the chamber for passage of the second adhesive component 81 therethrough. FIG. 26 shows a cross section across the inner and outer chambers 332, 334 and across the plunger 374.

Figure 28:
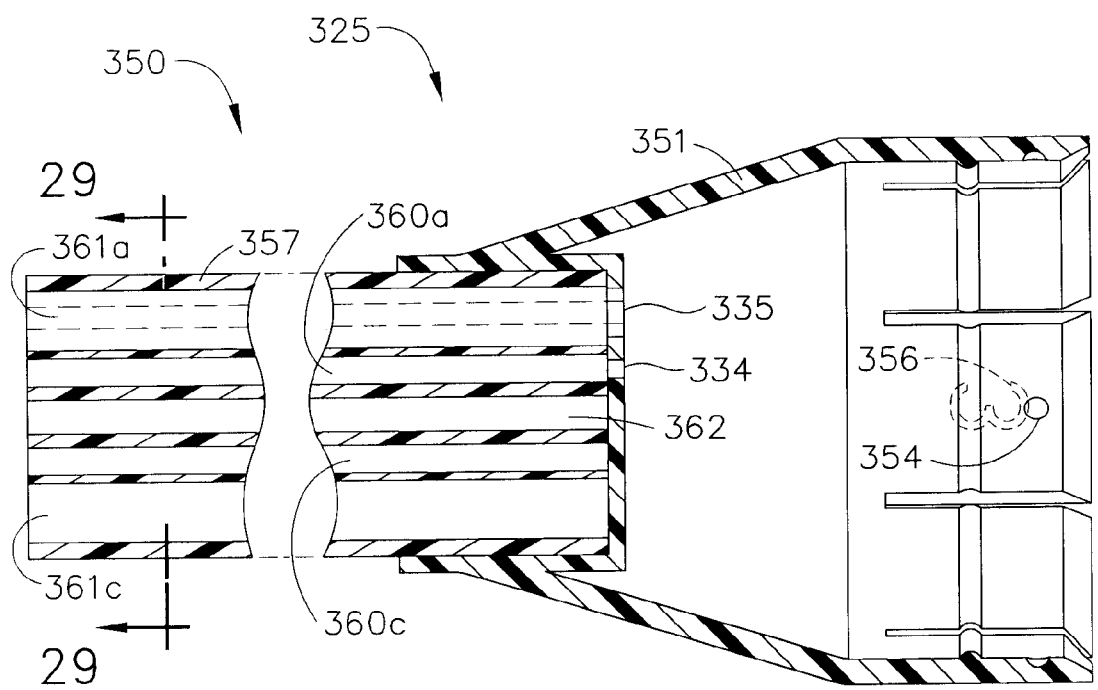
FIG. 28 is a side cross sectional view of the rotary nozzle of the alternate adhesive dispensing device of FIG. 24 showing a plurality of chambers therein and a detent to align an orifice with the two chambers of adhesive components.

As shown in cross section in FIGS. 24 and 28, a knob 351 of the indexing nozzle 350 can attach or snap onto a locking ridge 336 extending around the cylindrical body 330 and a locking groove 337 also extending around the body 330. The locking ridge and groove 336, 330 allow the indexing nozzle 350 to lock to and rotate about the cylindrical body 330. Alternately, if desired, the indexing nozzle 350 can be removable from the cylindrical body 330 and replaced with a fresh indexing nozzle 350.

Figure 27:
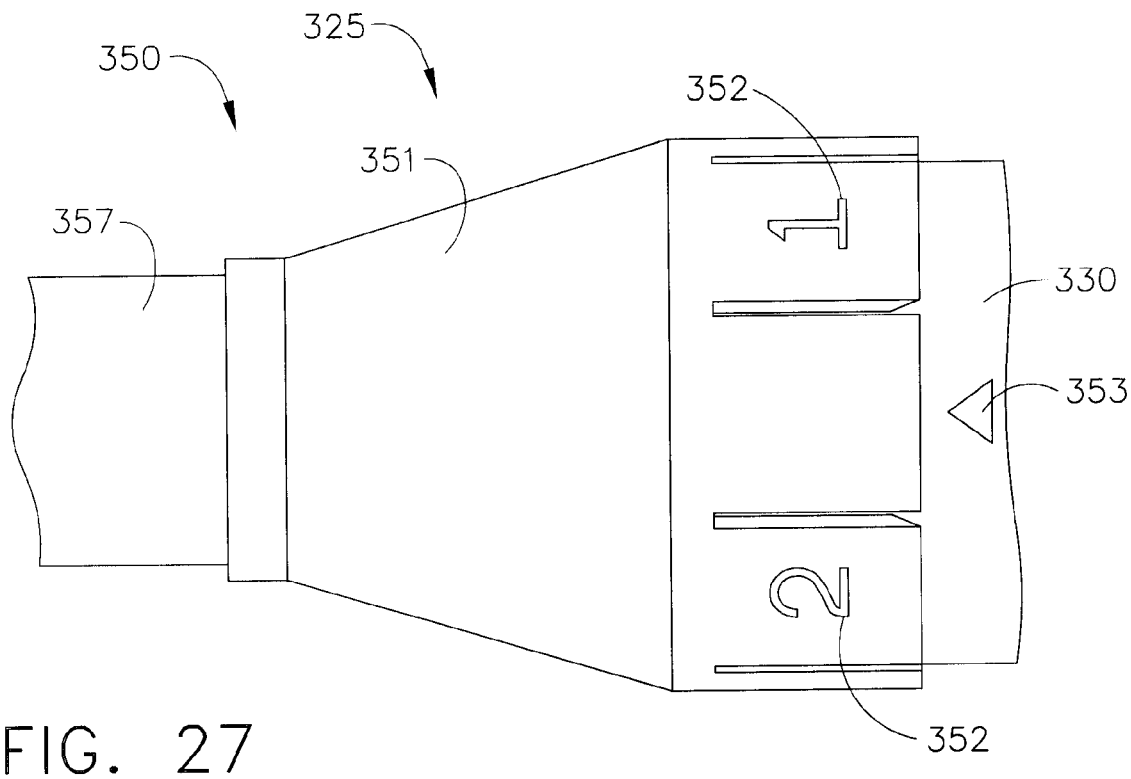
FIG. 27 is a side exterior view of the rotary nozzle of the alternate adhesive dispensing device of FIG. 24 showing indicia to align one of the plurality of orifices with the two chambers of adhesive components.

FIG. 27 can show an exterior view of the indexing nozzle 350 and the cylindrical body 330 showing a passive alignment system that uses numbers 352 on the rotatable knob 351 that can be aligned with a mark 353 on the body 330. The alignment of indicia can indicate alignment of passageways in the indexing nozzle 350 with the first bore 334 and second bore 335 enabling passage of adhesive components 80, 81 from the cylindrical body 330 into the aligned passageways.

FIG. 28 can show a cross sectional view of the rotatable knob 351 to show an active detent system that uses a bump 354 within the knob 351 that can engage with a series of depressions 355 (not shown) spaced about the cylindrical body 330. The active detent system uses the detent to indicate alignment of the passageways in the indexing nozzle 350 with the first bore 334 and second bore 335. This can enable passage of adhesive components 80, 81 from the cylindrical body 330 into the aligned passageways. If desired, indicia such as number 356 can be placed on the outside to indicate which set of passageways are being used. A cross section 29 is taken across a shaft 357 of the indexing nozzle 350 and shown in FIG. 29.

Figure 29:
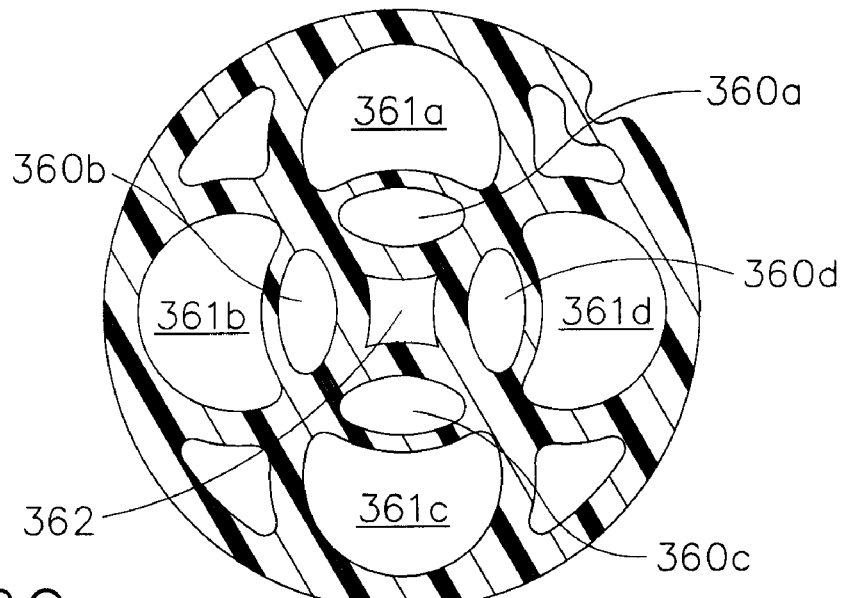
FIG. 29 is a first cross sectional end view of the rotary nozzle of the alternate adhesive dispensing device of FIG. 24 showing a plurality of chambers therein and a detent to align an orifice with the two chambers of adhesive components.
Figure 30:
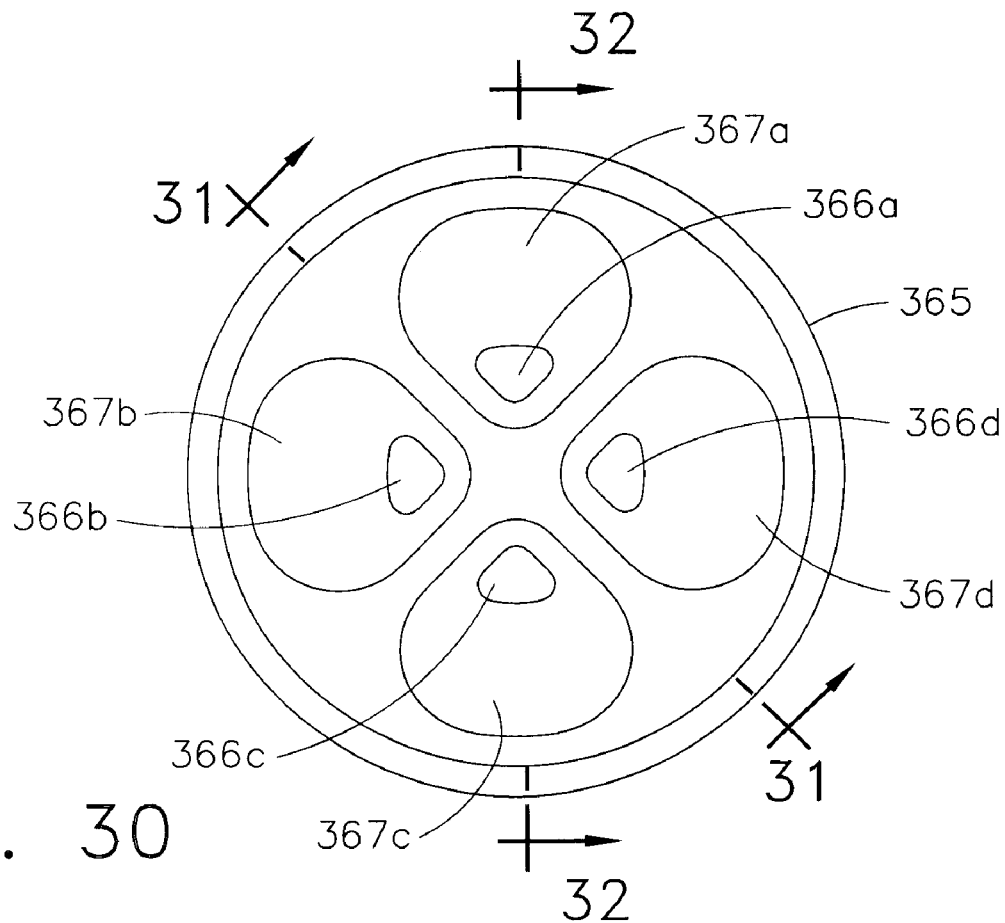
FIG. 30 is a second cross sectional end view of the rotary nozzle of the alternate adhesive dispensing device of FIG. 24.

In FIG. 29, the plurality of passageways through the shaft 357 can be seen. As shown, there are four smaller inner passageways 360a, 360b, 360c, 360d and four larger outer passageways 361a, 361b, 361c, 361d and a central passageway 362 extending longitudinally through shaft 357. As best shown in FIG. 24, the passageways 360a and 361a within shaft 357 are paired to align with the first bore 334 and the second bore 335 respectively of the cylindrical body 330 for the passage of first adhesive component 80 and second adhesive component 81 from chambers 332 and 333 respectively. The shaft 357 can form a seal with the first bore 334 and the second bore 335 to prevent egress of adhesive components 80, 81 therefrom or a secondary ring seal can be installed as required. In FIG. 24, it can be seen that the passageways 361c and 362c do not align with first bore 334 and the second bore 335 but could align if shaft 357 is rotated 180 degrees about central passageway 362.

A four passage tip 365 is conical and has four funnels 367a, 367b, 367c, 367d that align with four orifices 366a, 366b, 366c, 366d respectively and also align with passageways in shaft 357. Thus, each pair of inner and outer passageways align with a respective orifice. For example, as shown in FIG. 24, inner passageway 360a and outer passageway 361a align with funnel 367a to mix adhesive components 80, 81 therein and the mixed adhesive will then exit from orifice 366a.

Alternately, in other embodiments, the multi passage tip described above can be any shape provided it has plurality of orifices 366 for dispensing adhesive therefrom. For example, the tip 365 can be altered to be straight, tapered or flared to create any disbursing shapes such as but not limited to a fan. Alternately, for example, the tip 365 can also include attachment points for attachable detachable components such as but not limited to a brush, a swab and the like. Additionally the tip can have an orifice 368 that corresponds to central passageway 362. Passageway 362 and orifice 368 can provide an open passage from the knob 351 to the orifice 368 or can contain other devices. For example, passageway 368 can include or can contain a light for the polymerization or setting of the adhesive, a heater for the tip, a chiller for the tip, a light for visualization of the surgical site, a passageway for irrigation, a passageway for suction, a passageway for drug delivery, a power delivery shaft for adhesive mixing and dispensing, and an adhesive applicator to distribute the adhesive.

Figure 31:
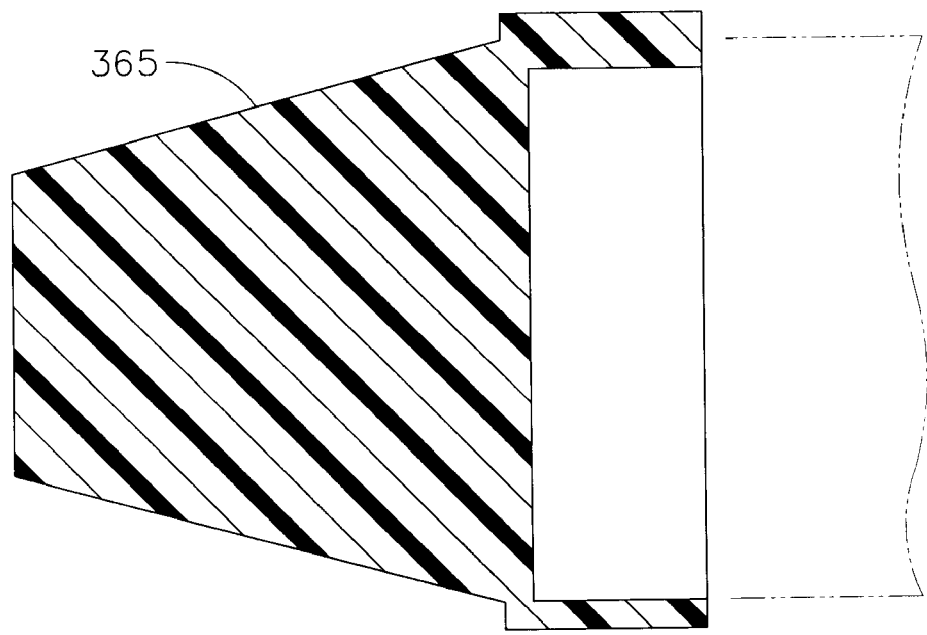
FIG. 31 is a first cross sectional side view across a diagonal of the rotary nozzle of the alternate adhesive dispensing device of FIG. 24.
Figure 32:
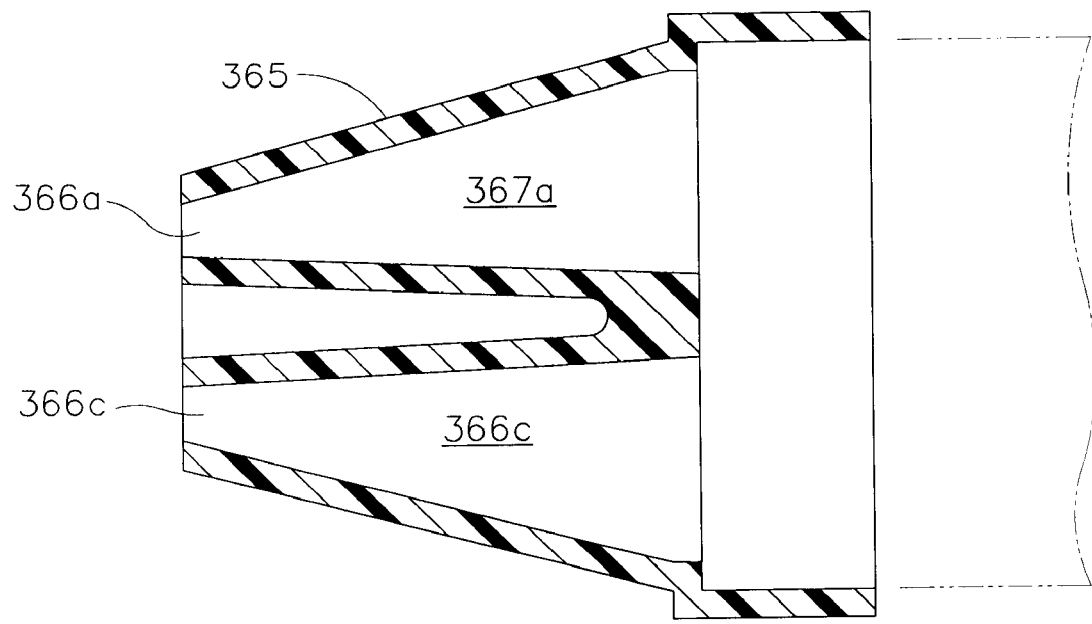
FIG. 32 is a second cross sectional side view of the rotary nozzle of the alternate adhesive dispensing device of FIG. 24.

FIG. 31 is a cross section taken through a cross member of the four passage tip 365. FIG. 32 is a cross section taken across the four passage tip 365 at an angle 45 degrees from the view of FIG. 31.

Many of the components above dispensing device 25, 325 must resist the adhesive effects of adhesive components 80, 81 that contact adhesive components 80, 81. Suitable engineering thermoplastic for adhesive contacting components such as the nozzles, shafts, mixers, plungers and the like can include but are not limited to polyethelene and polypropelene. Plunger materials can be elastomerics such as silicone, nitrile rubber and the like.

Adhesives

In the examples above, the adhesive is described as being composed of a first and a second adhesive components 80, 81. However, for example, the adhesive can also be a single component adhesive that can polymerize without an second adhesive component and the second adhesive component could be an adhesive polymerization accelerator. One example of a suitable adhesive component 81 could be a polymerizable cyanoacrylate adhesive. The adhesive 81, for example, may be but not limited to a monomeric (including prepolymeric) adhesive composition, a polymeric adhesive composition, or any other compound that can adhere to tissue and create a barrier to nutrient absorption. In embodiments, the monomer may be a 1,1-disubstituted ethylene monomer, e.g., an .alpha.-cyanoacrylate. When cross linked, the cyanoacrylate changes from a liquid to a solid adhesive. Cross linked adhesive can be a rigid or a flexible and can be non-permeable or permeable. If desired adhesive be a single part or dual part adhesive, and/or can contain additives 101. Alternately any other polymerizable adhesive components 81 can be used such as a polymerizable acrylic, epoxy or silicones. Any of the exemplary adhesive components 81 can be polymerized by a number of polymerization initiators such as but not limited to polymerization initiating compounds such as first adhesive component 80, light, Ultraviolet light, moisture, and tissue contact. For example, moisture and ultraviolet curing grades of adhesive 100 can include cyanoacrylates, acrylics, epoxies and silicones for forming adhesive fasteners.

Adhesive Initiators

Polymerization of the second adhesive component 81 can occur by mixing with the first adhesive component such as an adhesive initiator 300. Adhesive initiators 300 are for polymerization and/or cross-linking of a polymerizable monomer. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25 degree C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

Other suitable adhesives and, adhesive initiators 102, may be found in United States Application 20040190975 by Goodman et al. which is herein incorporated by reference in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, the above adhesive dispersement devices are not limited to the examples described above and can include any embodiments such as an array of selectable orifices that can be rotatably aligned with a glue dispersement mechanism can also be an array of orifices that can be linearly alignable with glue dispersement mechanism.

What is claimed is:

1. A surgical device for the mixing and dispensing of a dual component surgical adhesive onto tissue comprising:
    a) a handle;
    b) a first chamber containing a first adhesive component and a second chamber containing a second adhesive component, the first chamber and the second chamber located within the handle;
    c) a replaceable cartridge removably attached to the handle and having an empty third chamber and an empty fourth chamber and a mixing nozzle operably coupled to the third chamber and the fourth chamber, wherein when the replaceable cartridge is removably attached to the handle, the third chamber is operably attached to the first chamber and the fourth chamber is operably attached to the second chamber;
    d) a firing mechanism located within the handle and operably coupled to the replaceable cartridge when the cartridge is removably attached to the handle, wherein when the firing mechanism is actuated, a portion of the first adhesive component is drawn from the first chamber and into the third chamber, and a portion of the second adhesive component is drawn from the second chamber and into the fourth chamber, and the first portion of adhesive and the second portion of adhesive are mixed and ejected from the nozzle onto tissue; and
    e) a first valve system in the handle to provide one way passage of the first adhesive component from the first chamber and one way passage of the second adhesive component from the second chamber.

2. The surgical device of claim 1 further comprising a second valve system in the replaceable cartridge to provide one way passage of the first adhesive component from the third chamber and one way passage of the second adhesive component from the fourth chamber.

3. The surgical device of claim 1 further comprising an adhesive dispensing adjustment mechanism operably attached to the firing mechanism, the adhesive dispensing adjustment mechanism adjusting the amount of adhesive dispensed by an actuation of the firing mechanism.

4. The surgical device of claim 1 further comprising a gas assisted mixing system operably coupled with the disposable cartridge when the disposable cartridge is removably attached to the handle, wherein when the firing mechanism is actuated, the gas assisted mixing system delivers pressurized gas to the nozzle to mix the adhesive during ejection from the nozzle onto tissue.

5. The surgical device of claim 4 further comprising a gas canister in the handle and operatively connected to the firing mechanism to dispense gas when the firing mechanism is actuated.

6. The surgical device of claim 4 further comprising a hose connecting a pressurized gas source outside of the handle to the firing mechanism to dispense pressurized gas when the firing mechanism is actuated.

7. The surgical device of claim 1 further comprising a nozzle having a rotating mixer blade therein, wherein when adhesive enters the nozzle, the rotating mixer blade is rotated by the passage of the adhesive components and mixes the adhesive components prior to ejection from the nozzle onto tissue.

8. The surgical device of claim 1 further comprising a nozzle having a mixer spiral therein, wherein when adhesive enters the nozzle, contact of the adhesive with the spiral rotates and mixes the adhesive components prior to ejection from the nozzle onto tissue.

9. The surgical device of claim 1 wherein the first adhesive component is a polymer adhesive and the second adhesive component is a polymerization initiator.

10. The surgical device of claim 1 wherein the mixing nozzle is at least one selected from the group consisting of a flat fan nozzle, a tapered nozzle, a flared nozzle and a clear nozzle.

11. The surgical device of claim 1 wherein the mixing nozzle is removably attached to the handle for replacement of the mixing nozzle.

12. The surgical device of claim 1 wherein the first chamber comprises a first exit port, wherein the second chamber comprises a second exit port, wherein the mixing nozzle has a passive alignment system comprising indicia to indicate alignment of a selected orifice with the first exit port and the second exit port.

13. The surgical device of claim 1 wherein the first chamber comprises a first exit port, wherein the second chamber comprises a second exit port, wherein the mixing nozzle has an active alignment system comprising at least one detent to hold alignment of a selected orifice with the first exit port and the second exit port.

14. The surgical device of claim 1 wherein the first adhesive component is a polymer adhesive and the second adhesive component is a polymerization initiator.

15. The surgical device of claim 1 wherein the mixing nozzle has an open central passageway extending from the handle to the mixing nozzle and having a passageway orifice at a distal end.

16. A surgical device for the mixing and dispensing of a dual component surgical adhesive onto tissue comprising:
   a) a handle;
   b) a replaceable cartridge removably attached to the handle and having a first chamber containing a first adhesive component and a second chamber containing a second adhesive component, and a third chamber for the receipt of the first adhesive component and a fourth chamber for the receipt of the second adhesive component, and a mixing nozzle for the mixing and dispensing of the first adhesive component and the second adhesive component;
   c) a firing mechanism within the handle to draw the adhesive from the first and second chambers and into the third and fourth chambers and then mix and eject the adhesive components from the nozzle; and
   d) a gas assisted mixing system operably coupled with the replaceable cartridge when the replaceable cartridge is removably attached to the handle, wherein when the firing mechanism is actuated, the gas assisted mixing system delivers pressurized gas to the nozzle to mix the adhesive during ejection from the nozzle onto tissue.

17. The surgical device of claim 16 further comprising a gas canister in the handle and operatively connected to the firing mechanism to dispense gas when the firing mechanism is actuated.

18. The surgical device of claim 16 further comprising a hose connecting a pressurized gas source outside of the handle to the firing mechanism to dispense pressurized gas when the firing mechanism is actuated.

* * * * *